(12) United States Patent  
Steinert et al.

(10) Patent No.: US 8,052,674 B2  
(45) Date of Patent: Nov. 8, 2011

(54) LASER SYSTEM FOR VISION CORRECTION

(75) Inventors: Roger F. Steinert, Laguna Beach, CA (US); James W. Overbeck, Hingham, MA (US)

(73) Assignee: Roger F. Steinert, Laguna Beach, CA (US)

( * ) Notice: Subject to any disclaimer, the term of this patent is extended or adjusted under 35 U.S.C. 154(b) by 1269 days.

(21) Appl. No.: 11/102,985

(22) Filed: Apr. 11, 2005

(65) Prior Publication Data

US 2005/0278004 A1   Dec. 15, 2005

Related U.S. Application Data

(60) Provisional application No. 60/561,022, filed on Apr. 9, 2004.

(51) Int. Cl.  
*A61B 18/18* (2006.01)

(52) U.S. Cl. .................. 606/5; 606/4; 607/89

(58) Field of Classification Search .............. None  
See application file for complete search history.

(56) References Cited

U.S. PATENT DOCUMENTS

| | | | |
|---|---|---|---|
| 4,848,340 A * | 7/1989 | Bille et al. | 606/4 |
| 6,299,307 B1 * | 10/2001 | Oltean et al. | 351/210 |
| 2001/0016735 A1 * | 8/2001 | Frey et al. | 606/5 |
| 2003/0032950 A1 * | 2/2003 | Altshuler et al. | 606/9 |
| 2003/0123027 A1 | 7/2003 | Amir et al. | |
| 2004/0044333 A1 * | 3/2004 | Sugiura | 606/4 |
| 2005/0024586 A1 * | 2/2005 | Teiwes et al. | 351/209 |

FOREIGN PATENT DOCUMENTS

| WO | WO 01/28476 | 4/2001 |
|---|---|---|
| WO | WO 03/102498 | 12/2003 |

* cited by examiner

*Primary Examiner* — Sam Yao  
*Assistant Examiner* — Lynsey Crandall  
(74) *Attorney, Agent, or Firm* — Fish & Richardson P.C.

(57) ABSTRACT

A laser system for treating an eye having a cornea, the laser system including a laser beam source capable of generating a laser beam, an eye position detector which includes at least a corneal tracker, the corneal tracker being responsive to movement of an anterior portion of the cornea, the corneal tracker constructed to detect movement of the cornea based on a set of spaced apart optical manifestations from the outer surface of the anterior portion of the cornea, and a beam controller, the beam controller being responsive to the eye position detector to direct the laser beam with controlled energy from the laser beam source to a desired location on the eye.

18 Claims, 17 Drawing Sheets

$X_{44}$ = Distance From Center Line to Center of Pupil.

$X_{55}$ = Distance From Center Line to Midway Point Between Reflections of Lights A & B.

W = DisTANCE From Center Line to Center of Surface of Cornea

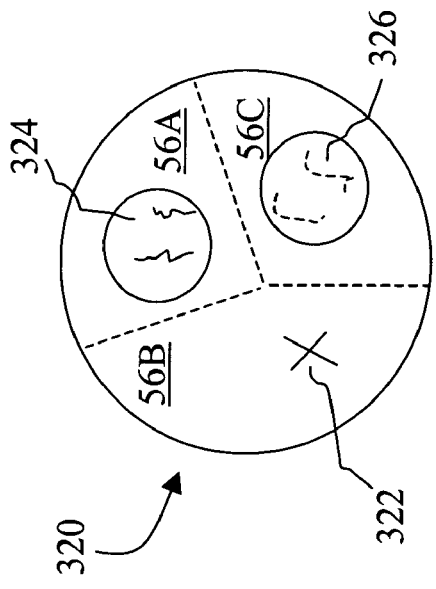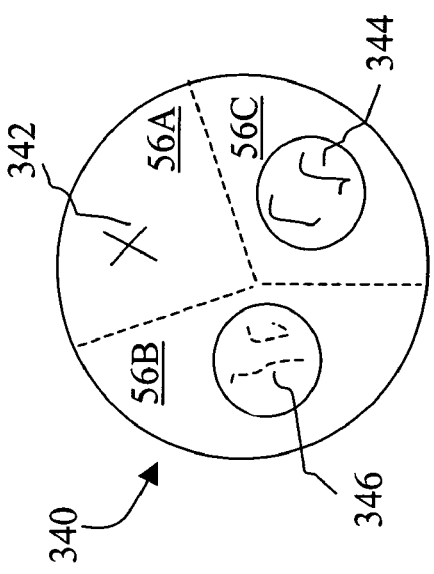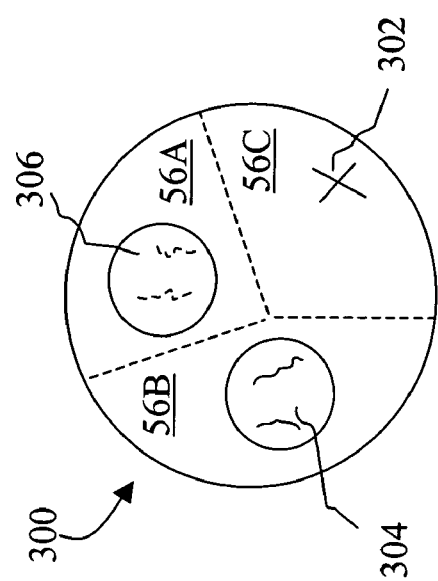

LASER SYSTEM FOR VISION CORRECTION

CLAIM OF PRIORITY

The present application claims the benefit of U.S. provisional application No. 60/561,022, filed Apr. 9, 2004, which is incorporated herein by reference.

TECHNICAL FIELD

This disclosure concerns laser systems for treating the eye, with special applicability to improving the optical quality of laser treatment of the cornea for vision correction. It relates to procedures such as photo refractive keratotomy (PRK), laser treatment performed under a corneal flap such as Laser in Situ Keratomileusis (LASIK), procedures performed under an epithelial flap (LASEK), and other laser procedures. The disclosure is directed to initial referencing the laser treatment on the cornea, to maintaining alignment of the treatment beam during the procedure, and to depositing the prescribed energy at desired location on the cornea despite roll of the eye.

BACKGROUND

Laser systems for treating the eye involve directing an energetic laser beam upon the cornea to remove corneal tissue by the process known as ablation. Excimer lasers are typically employed. Maintaining the relationship of each instant of laser energy deposition relative to previous depositions is important to produce the desired conformational change across the treated corneal area. In order to maintain registration, tracking systems have been employed based on the pupil and iris of the eye.

One established excimer laser system has an iris tracking system employing small, low energy tracking beams, to track the edge of a fixed and dilated pupil using a dedicated edge detection system. Four infrared beams scan back and forth in radial fashion at different quadrants of the round pupil, each detecting a signal difference as the beam crosses the edge of the dark pupil onto the iris. The pupil is typically required to be dilated and not moving. A clinical strategy for employing this technique first captures a video digital image of the non-dilated eye when the patient is fixated on a spot, such as on a blinking red light. The limbus and/or other anatomical landmarks are identified by a human operator, and a computer-generated image of a ring is imposed on the limbus on the computer screen. Using that ring, the laser surgeon then locates a yellow-cross-hair in the center of the pupil as a reference for the treatment. The patient then is taken from the treatment station, administered a drug to dilate the pupil, and when stable dilation is achieved, the patient returns for laser treatment. With the tracking system activated, the computer-captured-ring from the pre-dilation state is imposed on the image of the limbus of the dilated eye, when fixated as before. This locates the yellow cross-hair, representing the pupil center in the same position as before dilation. Though the pupil is dilated to larger, fixed size, the laser surgeon, knowing the center of the undilated pupil, can conduct the procedure with that reference.

A system along that line is disclosed in U.S. Pat. No. 5,740,803, hereby incorporated by reference.

In another established laser treatment system, the front of the eye is flooded with infrared (invisible) light to detect the transition between the iris, which significantly reflects the infrared light, and the pupil, which is relatively absorptive of the infrared light. An infrared sensitive photo detector measures the reflected infrared light. On the assumption that the pupil is round, the computer performs edge detection to determine best fit and mathematically solves the equation to determine the center of the round circle determined from the detected data. This system allows the pupil to be smaller and to vary somewhat in size during treatment, employing the assumption that the pupil expands and contracts concentrically. As long as the eye is concentric and moves within a relatively modest range, e.g. between 2 and 4 millimeters, the mathematical solution for the center of the circle remains essentially at the same spot and the treatment remained centered.

In further proposed systems, pattern recognition techniques have been proposed for detecting the iris, by which the center and orientation are determined, from which the desired corrections are referenced.

Besides such prior systems that conduct laser treatment based on an image of the iris of the eye in the X,Y plane, other proposals have concerned tracking other gross features such as the incision line of a turned corneal flap, or of using techniques based on optical features internal of the eye.

SUMMARY

The invention provides precision tracking based on optical manifestations from the curved outer surface of the cornea. For example, the tracking can be used to compensate for voluntary or involuntary rolling motion of the eye.

In one aspect, the invention features a laser system for treating an eye having a cornea, the laser system including a laser beam source capable of generating a laser beam, an eye position detector which includes at least a corneal tracker, the corneal tracker being responsive to movement of an anterior portion of the cornea, the corneal tracker constructed to detect movement of the cornea based on a set of spaced apart optical manifestations from the outer surface of the anterior portion of the cornea, and a beam controller, the beam controller being responsive to the eye position detector to direct the laser beam with controlled energy from the laser beam source to a desired location on the eye.

Embodiments may include one or more of the following. The laser beam source is constructed to produce a beam capable of ablating corneal tissue. The corneal tracker is constructed and arranged to detect rolling rotation of the eye, in some examples the beam controller includes a laser energy deposition controller, the laser energy deposition controller being constructed and arranged to deposit energy at selected levels at respectively designated positions on the anterior portion of the cornea, the deposition controller being responsive to detected rolling rotation of the eye to correlate the level of energy deposition with the actual position of the eye. In some of these examples, the laser system includes a laser source, the laser source being fixed and the beam controller being constructed to respond to rolling rotation of the eye to adjust the level of energy being deposited based on change in the angle of presentation of a target portion of the corneal surface due to the rolling rotation. In other examples, the eye position detector includes a translation tracker constructed and arranged to cooperate with the corneal tracker to adjust the aim of the laser beam. In some examples, the laser system is constructed, in absence of eye roll, to determine the position of the laser beam in response to the translation tracker. In other examples, the translation tracker is an iris tracker that is constructed and arranged to track the translated position of the iris.

Embodiments may also include one or more of the following. The laser system further includes an observation system having a display screen, the observation system enabling the operator to observe a display of the translation-determined position of the laser beam on an image of the cornea, the laser system comprising an offset arrangement to cause the point of incidence of the laser beam on the eye to be offset in X and Y coordinates, relative to the display screen, in an amount controlled by rolling rotation data from the corneal tracking system. Referring to X, Y and Z spatial coordinates in which Z represents the axis of the treatment beam, the translation tracker is adapted to produce X and Y iris-based beam control values and a visual representation of the aim of the laser beam relative to the iris, and the corneal tracker is responsive to rolling rotation of the eye to produce X and Y corneal-rolling rotation-based control values representing the difference in true position of the desired treatment axis relative to its position approximated by the iris-based control values, the laser system responsive to the iris-based and corneal-rolling rotation-based beam control values to direct the laser beam to a position on a portion of the cornea anterior of the iris that is offset from the visual representation of the aim of the laser beam relative to the iris. In some examples, a pair of X, Y galvanometers controlled by the iris-based control values are arranged to deflect the laser beam from the laser beam source, a beam splitter is arranged to direct portions of the deflected beam respectively toward the eye and toward an imaging device for the visual representation of the aim of the laser beam, and a second pair of X, Y galvanometers controlled by the corneal-rolling-rotation based beam control values are positioned to redirect one portion of the deflected beam to provide the offset due to eye rolling.

Embodiments may also include one or more of the following. The laser system includes a pattern of spaced apart light source regions positioned to be reflected as a specular pattern from the outer surface of the cornea back to the corneal tracker. In some examples, the laser system includes at least two spaced apart light sources each capable of radiating toward the eye over an angular range, to illuminate the cornea, the light sources being spaced from the axis of the laser beam and from each other in a pattern enabling rolling rotational displacement of the reflections to be resolved in orthogonal components normal to the longitudinal axis to produce control values. In some of these examples, there are at least three spaced apart light sources arranged in a polygonal pattern. The laser system can also include an iris tracker capable of producing an image of the iris and of the pattern of spaced apart light source regions, the laser system constructed and arranged so that, in the absence of rolling rotation of the eye, translation movement of the eye does not substantially displace the reflected light source image relative to the image of the iris. The iris tracker has dedicated scanners that detect the iris-to-pupil transition at least at three positions spaced about the periphery of the pupil, and is adapted to derive there from an estimated position for the center of the treatment. The iris tracker includes an imager for imaging peripheral portions of the pupil and adjacent portions of the iris, and the iris tracker is adapted to derive from the imager an estimated position for the center of the treatment. The laser system is operative, in absence of eye rolling, to position the laser beam in response to the iris-translation tracker. The iris-translation tracker includes an imaging and pattern recognition system for imaging at least a portion of the iris in a plane, and the imaging and pattern recognition system estimates from a pattern of the image a position for the center of the treatment and an estimation of any rolling rotation of the iris in the plane.

Embodiments may also include one or more of the following. The corneal tracker is constructed and arranged to select and track motions of a set of microscopic, visible details on the outer surface of the cornea, the set defining a pattern in X, Y coordinates. In some examples, the corneal tracker is constructed and arranged to select and track motion of at least two sets of the visible details on the outer surface of the cornea, and to shift from dependence on a first of the sets to a second of the sets when a region of the first set becomes a target region for the laser beam, and to operate in iterative fashion, acquiring a successive set while abandoning the first set in the manner that the corneal tracker at substantially all times has acquisition of at least one set that is not being disturbed by the laser. In some examples, the corneal tracker uses an estimated radius of curvature of the cornea to produce the X and Y corneal-rolling rotation-based control values and if the laser system changes the radius of curvature, the corneal tracker updates the estimated radius of curvature as the laser system changes the radius of curvature.

In another aspect, the invention features a laser system for treating the eye, the system including a laser beam source capable of producing a laser beam, an eye position detector which includes at least a corneal tracker responsive to movement of an anterior portion of cornea of the eye, the corneal tracker being constructed, by pattern analysis, to track a pattern of microscopic visible features of the anterior corneal portion within the bounds of a polygon, and a beam controller, the beam controller being responsive to the eye position detector to direct the laser beam with controlled energy from the beam source to a desired location on the eye.

Embodiments may include one or more of the following. The corneal tracker is constructed to use pattern analysis to independently track at least two spaced apart patterns of microscopic visible features of the anterior corneal portion, and to base instantaneous tracking values from instant to instant on at least one pattern in a region not, at the respective instant, being treated by the laser beam.

Embodiments of the invention may have one or more of the following advantages. More accurate laser eye surgery can be performed using tracking of the outer corneal surface compared to tracking using features that are posterior to the surface. This is because eyes can roll during surgery and because the corneal surface is not concentric with the center of rolling motion such that the resulting error limits the accuracy of laser eye surgery using tracking of posterior features.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 7A is a magnification of a portion of FIG. 7.

FIGS. 9A, 9B, and 9C are diagrams representing different states during surgery using the laser system of FIG. 8.

Like reference symbols in the various drawings indicate like elements.

DETAILED DESCRIPTION

Figure 1:
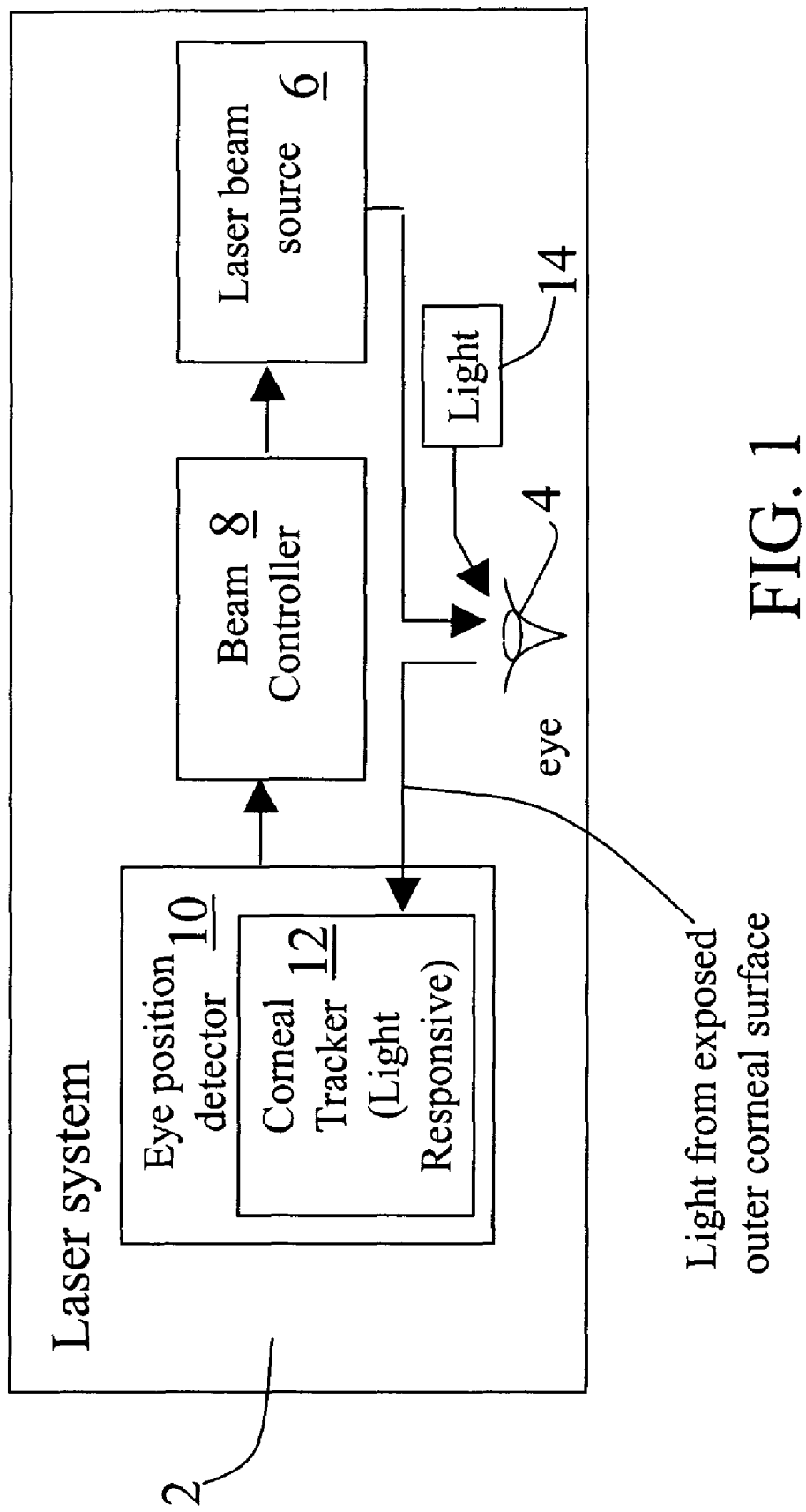
FIG. 1 is a block diagram of a laser system for eye treatment, the laser system having a corneal tracker.

Referring to FIG. 1, a laser system 2 performs treatment of an eye 4. The laser system 2 includes a laser beam source 6 that is controlled by a beam controller 8 that responds to an eye position detector 10. Eye position detector 10 measures the position of the eye 4 relative to a nominal position with respect to the laser beam source 6. The beam controller 8 is constructed to use information from the eye position detector 10 to reference the positioning of the laser beam from the source 6 during surgery.

The eye position detector 10 includes a corneal tracker 12 that is responsive to optical manifestations from the outer surface of the anterior portion of the cornea of the eye 4. The corneal tracker 12, by sensing a more accurate position of the cornea, is used to avoid errors that would occur when the eye 4 is rolled if translation of the iris were the control parameter. The optical manifestations may be, for example, reflections of light from undirected light sources resulting from diffuse light or a pattern of microscopic optical features of the surface of the cornea. In some cases, the outer surface of the anterior portion of the cornea from which the manifestations are obtained is the exposed surface after the top layer of the corneal epithelium (the "flap") is moved aside such as for Laser in Situ Keratomileusis (LASIK) surgery. In other cases, the outer surface of the anterior portion of the cornea is the exposed natural outer surface of the cornea, such as for Photo Refractive Keratotomy (PRK). This outer surface of the anterior portion of the cornea is the area that would be moved aside if LASIK surgery were to be performed.

Figure 2:
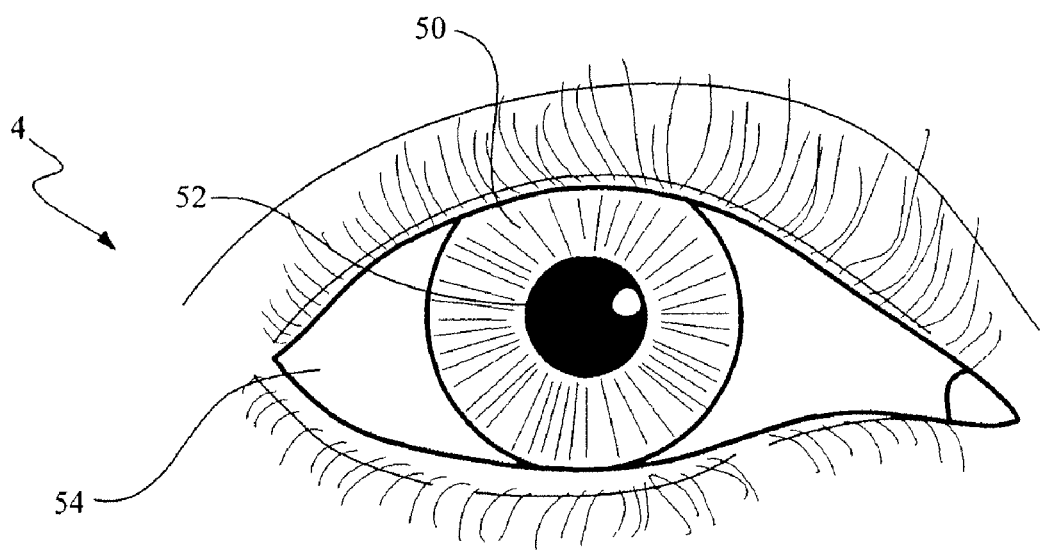
FIGS. 2 and 2A are illustrations of an eye.
Figure 2A:
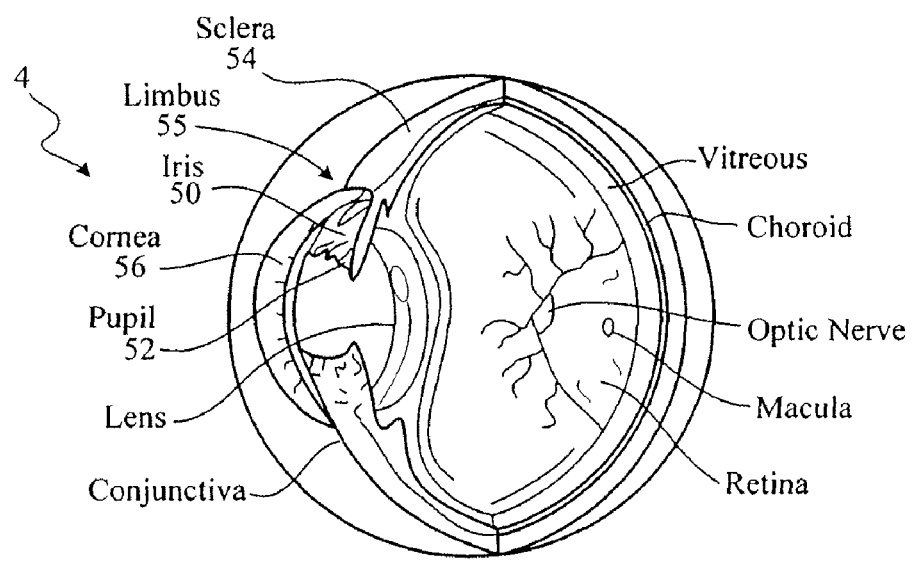

Referring to FIG. 2, a view along the optical axis, iris 50, pupil 52, and sclera 54 of eye 4 are shown. Referring to FIG. 2A, cornea 56 overlying the pupil 52 and the iris 50 is shown. It is well known that the center of curvature of the cornea 56 is significantly offset from the center of the eye ball.

Figure 3A:
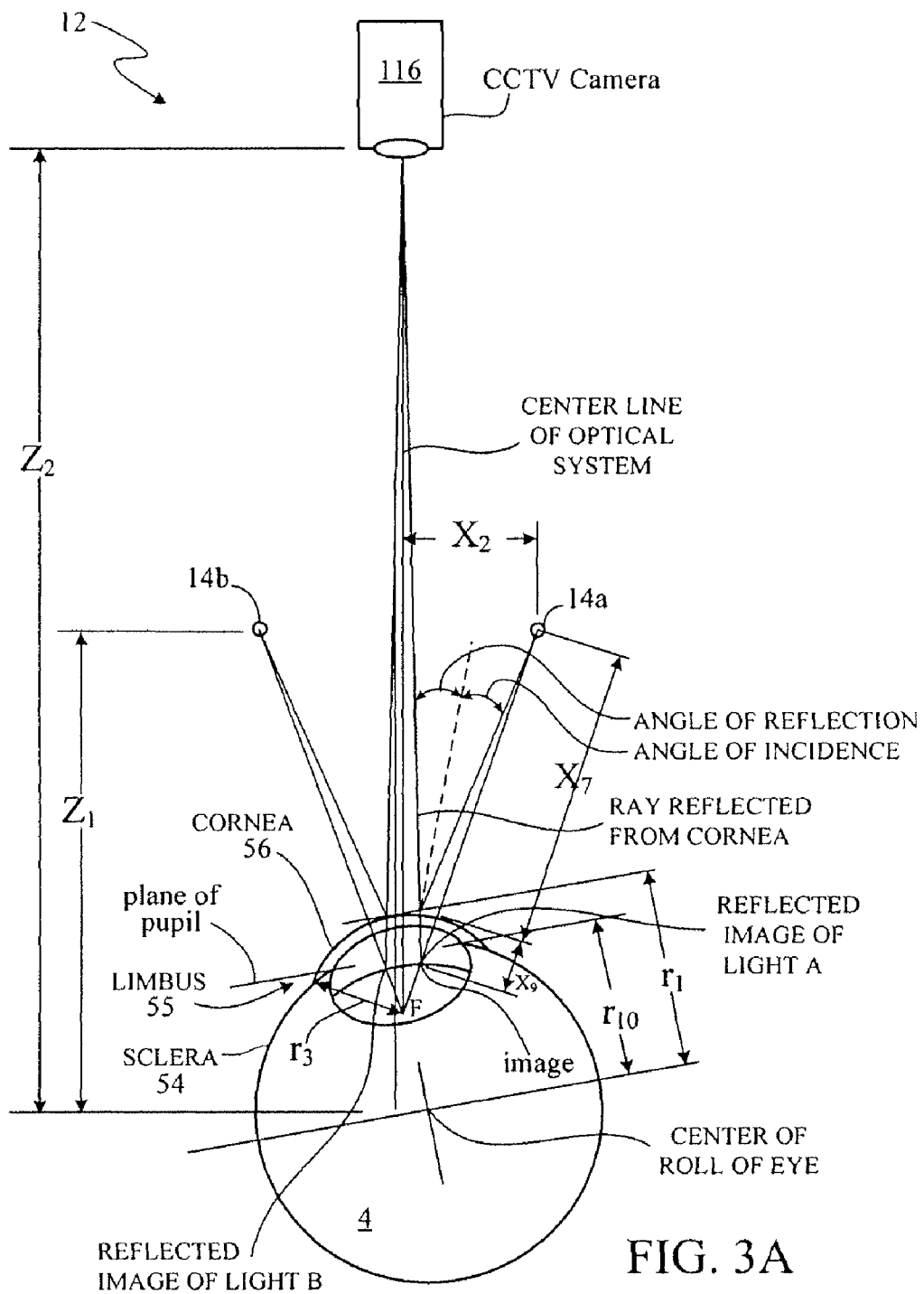
FIG. 3A is a diagrammatic representation of a corneal tracker measuring the displacement of the center of a cornea.

Referring to FIG. 3A, an example of the corneal tracker 12' uses a CCTV camera 116 to track the position of the center of the cornea 56. In this figure, two stationary spaced-apart light sources 14a, 14b shine light toward the eye 4. One or more additional spaced-apart light sources are used for concrete tracking of the cornea 56, for instance four light sources may be arranged in a square or other pattern, and the calculations now to be described may be performed with respect to each pair of light sources and the results combined to determine the treatment center. The corneal tracker 12' tracks the reflections of the light sources 14a, 14b from the cornea 56 using well known image processing techniques. The reflection from the outer surface of the cornea 56, with corneal radius of curvature $r_3=8$ mm, is equivalent to viewing the eye 4 through a negative focal length lens with focal length=$FLR=-r_3/2=-4$ mm. The distance $x_9$ from the surface of the cornea 56 to the image of light $14a=FLR*x_7/(x_7-FLR)$, where $x_7$=distance from light 14a to the surface of the cornea 56. $x_7$=approximately $z_1-r_1=288$ mm. $x_9=3.945$ mm.

Figure 3B:
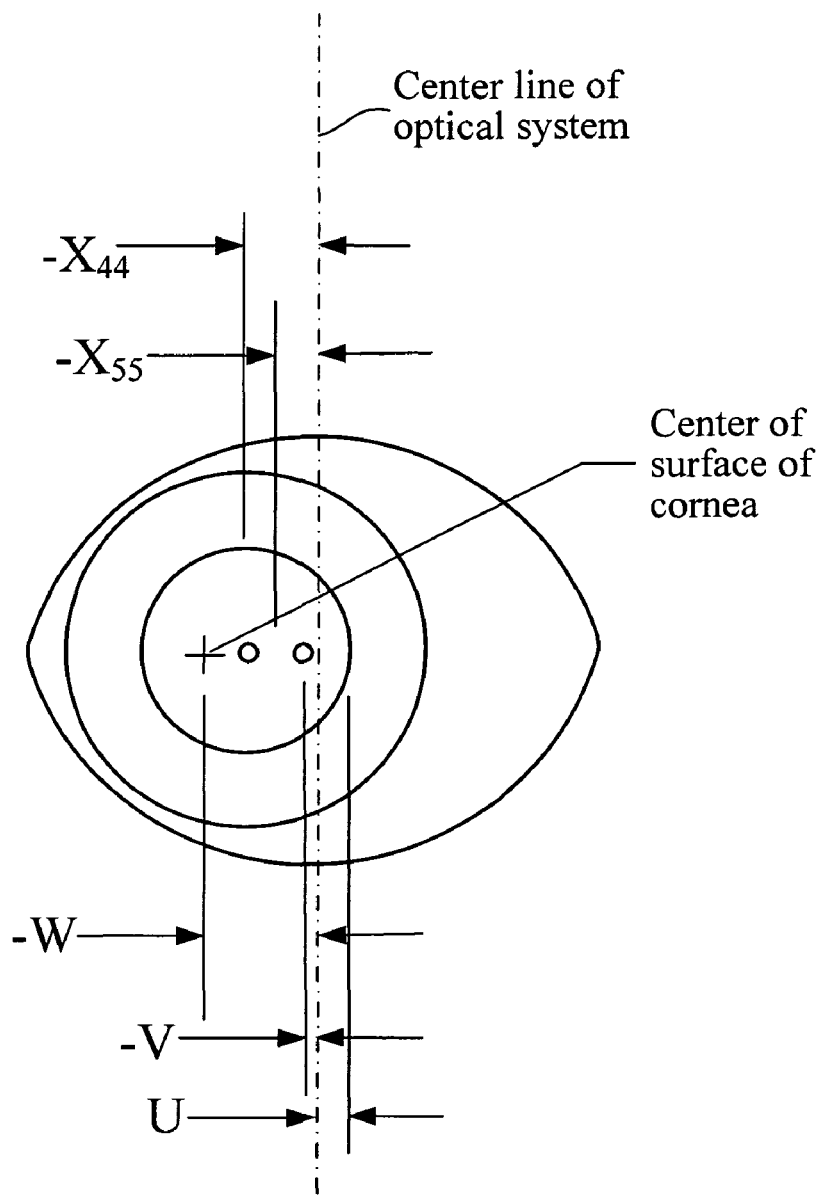
FIG. 3B is a diagram of a rolled eye with reflections from a corneal tracker.

Referring to FIG. 3B, W is the position of the center of the cornea 56 relative to the optical axis of CCTV camera 116. U is the position of an edge of the pupil 52, as seen by the CCTV camera 116 (at a finite distance, $z2-r1$, from the surface of the cornea 56). V is the position of the center of the reflection of light 14a from the surface of the cornea 56.

$$W=A*(u-r_4)+B*(v-(r_3-x_9)*x_2/(r_3+x_7)), \text{ where}$$

$A=C-r_1*D$
$B=E-r_1*F$
$C=1/(G-H*I/J)$
$D=1/(H-G*J/I)$
$E=1/(I-J*G/H)$
$F=1/(J-I*H/G)$
$G=z_2/(z_2-r_2)$
$H=-z_2*r_2/(z_2-r_2)$
$I=(2*x_9/r_3)*(z_2/(z_2-r_1+x_9))$
$J=-(r_1-r_3)*I$

Figure 3C:
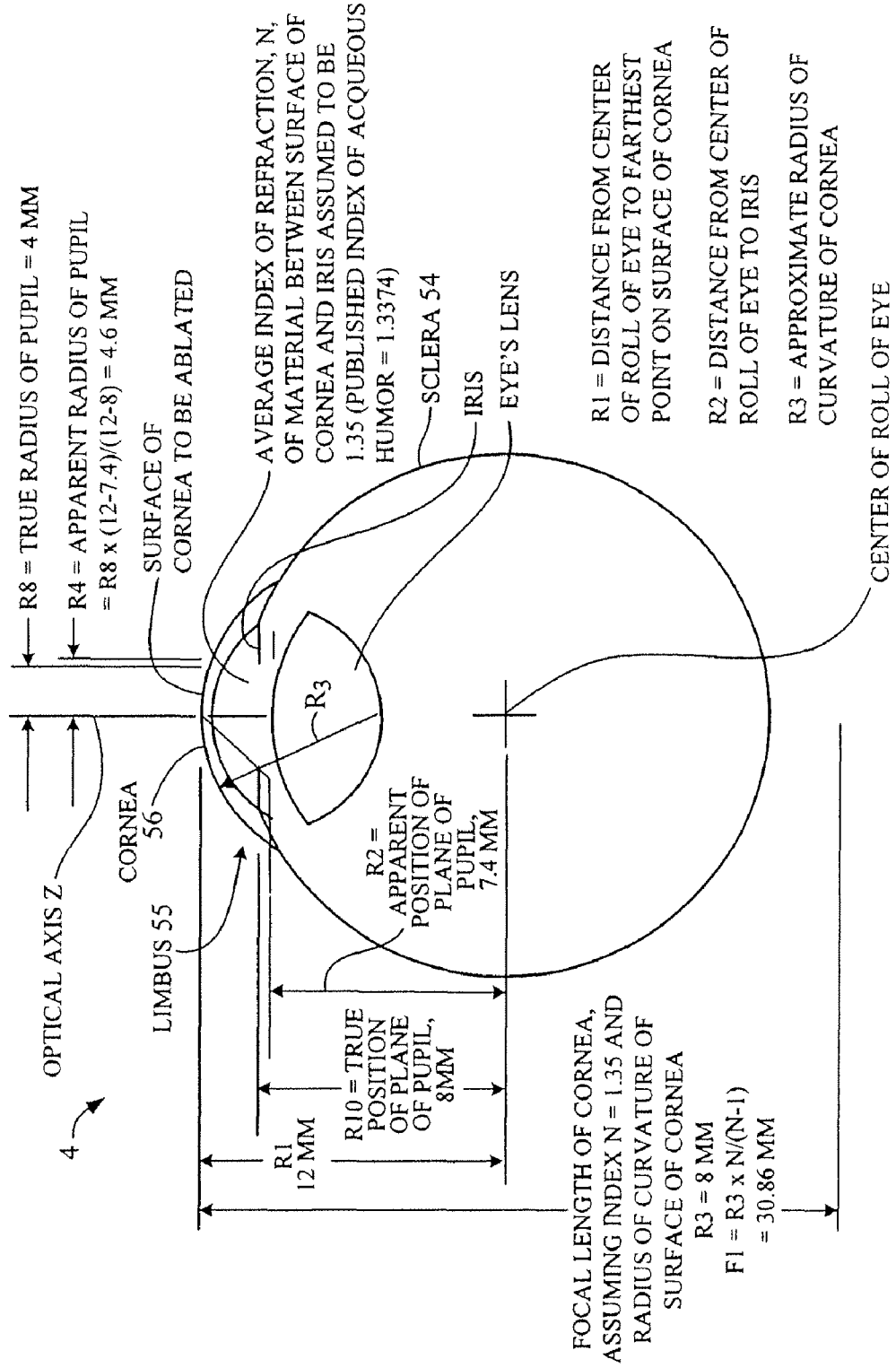
FIG. 3C is a diagram representing variables for corneal tracking.

Referring to FIG. 3C, the meanings of the parameters $r_1$, $r_2$, $r_3$, $r_4$, etc. are:

$r_1$=distance from center of the eye 4 to outer surface of the cornea 56.
$r_2$=apparent distance from center of eye to plane of the pupil 52.
$r_3$=radius of curvature of the cornea 56.
$r_4$=apparent radius of the pupil 52.
$z_1$=vertical distance from center of the eye 4 to light 14a (or 14b).
$x_2$=horizontal distance from center line of optical system to light 14a (or 14b).
$z_2$=vertical distance from center of eyeball to lens of CCTV camera 116.
$x_7=\sqrt{(z_1-r_1)^2+x_{22}}$=distance from surface of the cornea 56 to light 14a (or 14b).
$x_9=x_7*r_3/(r_3+2*x_7)$=distance from surface of cornea to reflected image of light 14a (or 14b).

The "apparent" distances $r_2$ and $r_4$ differ from the true distances $r_8$ and $r_{10}$, because of the lens effect of the curved surface of the cornea 56.

$r_8$=the true radius of the pupil 52.
$r_{10}$=the true distance from center of the eye 4 to the plane of the pupil 52.
$f_1$=the focal length of the surface of the cornea $56=r_3*n/(n-1)$, where n=index of refraction of the cornea 56.
$r_2=r_1-f_1*(r_1-r_{10})/(f_1-r_1+r_{10})$
$r_4=r_8*(r_1-r_2)/(r_1-r_{10})$ In order to be insensitive to the diameter of the pupil 52, the corneal tracker 12' measures the position $x_{44}$ of a point midway between opposing edges of the pupil 52.

The calculation of the position of the opposing edge of the pupil 52 is the same as the calculation for W except that $r_4$ is replaced by $-r_4$. Note that $r_4$ appears only in the last equation for W above.

Similarly, in order to be less sensitive to the radius of curvature of the cornea 56, the corneal tracker 12' measures the position $x_{55}$ of a point midway between the reflections of lights 14a and 14b.

The position of light 14b is calculated by changing $x_2$ to $-x_2$ in the above calculation. Note that $x_2$ also appears only in the last equation for W above.

Accordingly, $W = A^* x_{44} + B^* x_{55}$.

Typical values of the parameters, and corresponding values of variables A through J are:

$r_1 = 12.0$ nm
$r_2 = 7.4043$ nm
$r_3 = 8.0$ mm
$r_4 = 4.5957$ mm
$r_8 = 4.0$ mm
$r_{10} = 8.0$ nm
$x_2 = 75.0$ mm
$x_7 = 297.60544$ mm
$x_9 = 3.9470$ mm
$z_1 = 300.0$ mm
$z_2 = 500.0$ mm
$n = 1.35$
$f_1 = 30.8571$ mm
$A = 2.35$
$B = -1.36814483$
$C = -1.175$
$D = -0.29375$
$E = 2.20423334$
$F = 0.29769818$
$G = 1.0$
$H = -7.40425532$
$I = 0.98673764$
$J = -3.94695056$

Figure 3D:
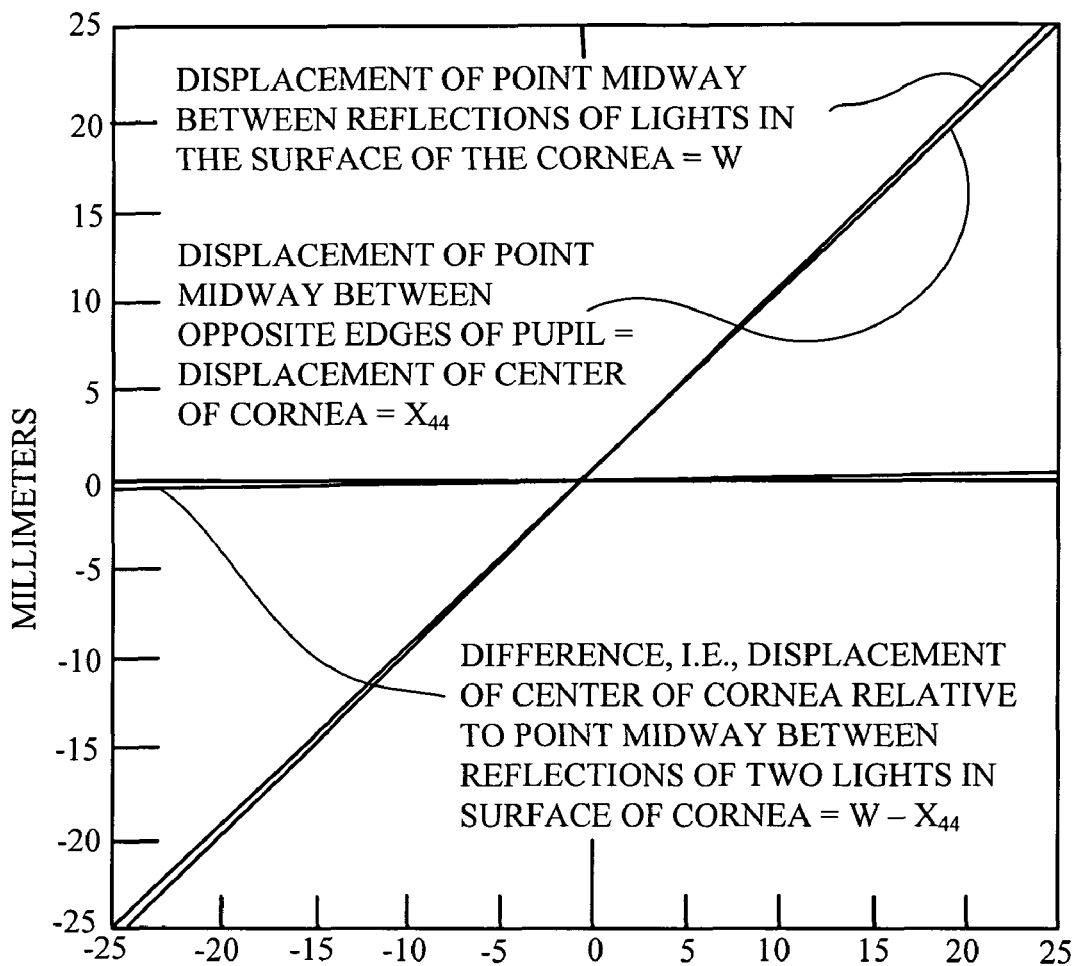
FIG. 3D is a graph of the difference between positions of reflected light from the outer surface of a cornea and positions of the center of a pupil when an eye is translated.

Referring to FIG. 3D, when the motion of the eye consists only of a translation and there is no roll of the eye 4, then the translation $x_{44}$ of the center of the pupil 52 is equal to the translation W of the center of the cornea 56. There is only a small (0.33 mm) displacement of the reflections of light in the surface of the cornea 56 (relative to the center of the pupil 52) when the eye 4 is translated 25 mm. Thus it is shown that tracking the pattern of reflections can be an effective substitute for tracking the pupil for detecting translation.

Figure 3E:
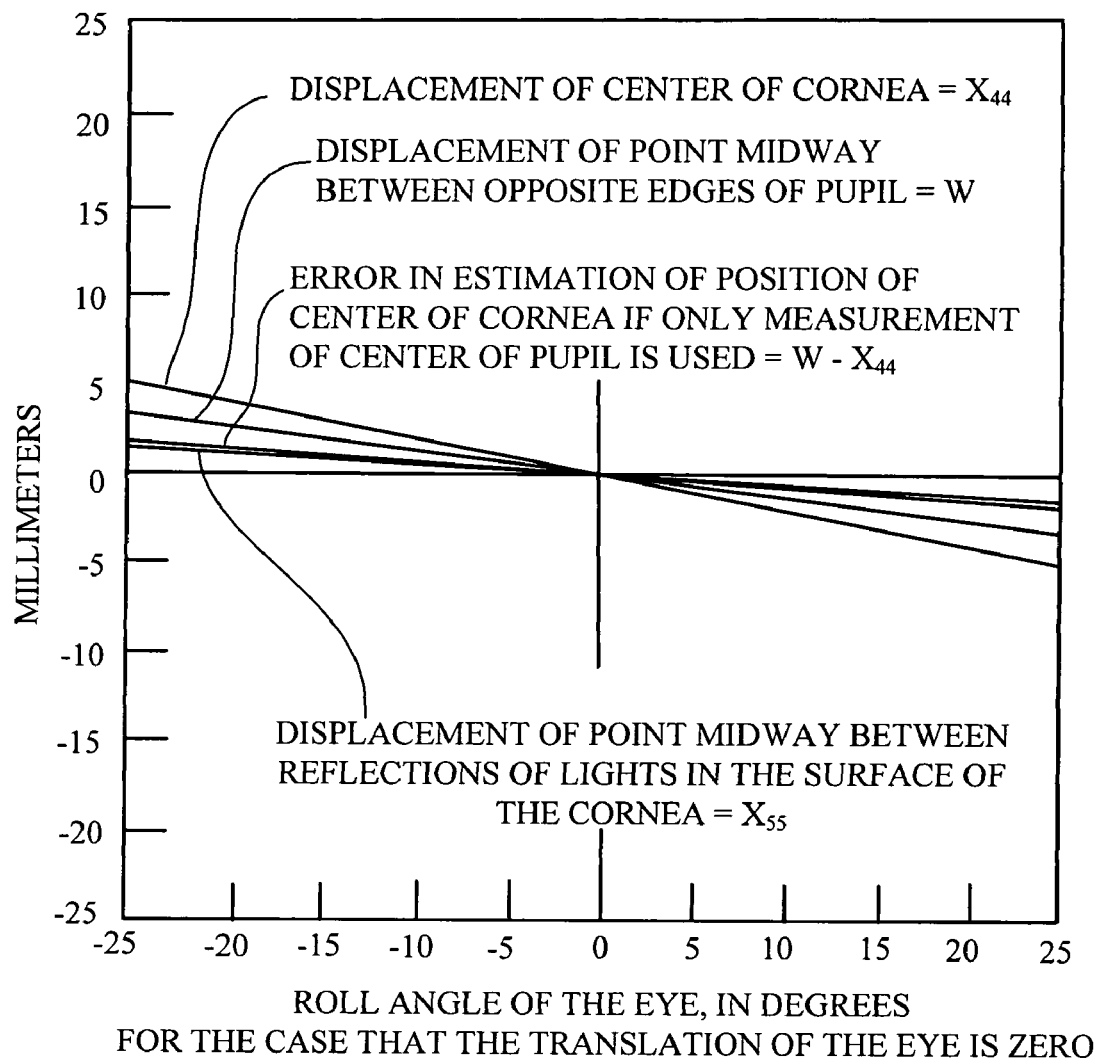
FIG. 3E is a graph of the difference between positions of reflected light from the anterior surface of a cornea and positions of the center of a pupil when an eye is rolled.

Referring to FIG. 3E, when the eye 4 rolls, rather than translates, the measurement of the position $x_{44}$ of the pupil 52 differs from the position W of the center of the cornea 56 by $W - x_{44} = 2$ mm when the roll angle is 25 degrees. The position $x_{55}$ of the point midway between the two reflections of light in the surface of the cornea 56 increases as the eye 4 rolls.

In general, the motion of the eye 4 consists of a translation and a roll. In the general case, the displacements of the cornea 56, the pupil 52, and the reflections of the lights 14a, 14b from the surface of the cornea 56 are the sum of the values shown in FIGS. 3B and 3C. Thus, it is shown that the tracked light pattern accurately indicates the position of the center of the cornea 56 with respect to both translation and roll of the eye 4.

Figure 3F:
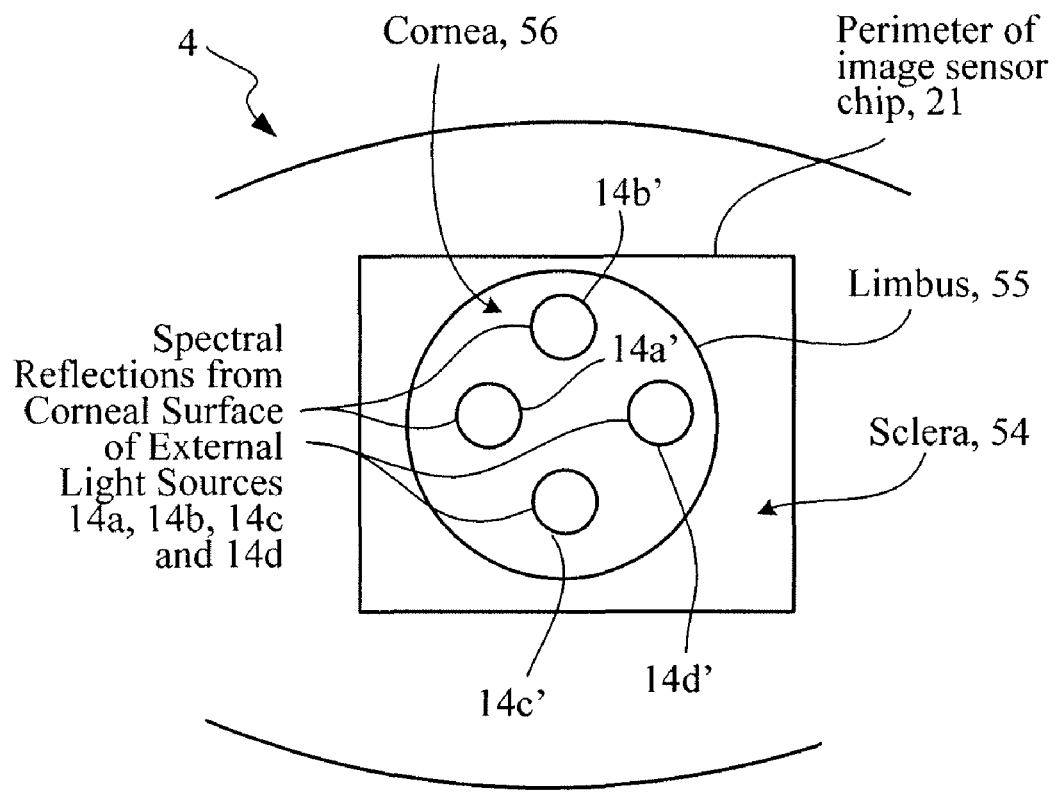
FIG. 3F is a diagram of a perimeter of an image sensor chip superimposed upon a cornea for corneal tracking.

In one example, referring to FIG. 3F, the corneal tracker 12' includes four light sources, in a square pattern, having reflections 14a', 14b', 14c', and 14d' from the anterior surface of the cornea 56. The corneal tracker 12' includes a high speed CMOS image sensor chip with a small number of pixels. For example, the CMOS image sensor chip LM 9630 provides an imaging window 21 of 96 by 118 pixels. The CMOS image sensor chip LM 9630 is available from National Semiconductor. The LM 9630 enables readout of an entire 96 by 118 pixel image in less than 2 milliseconds.

Figure 4:
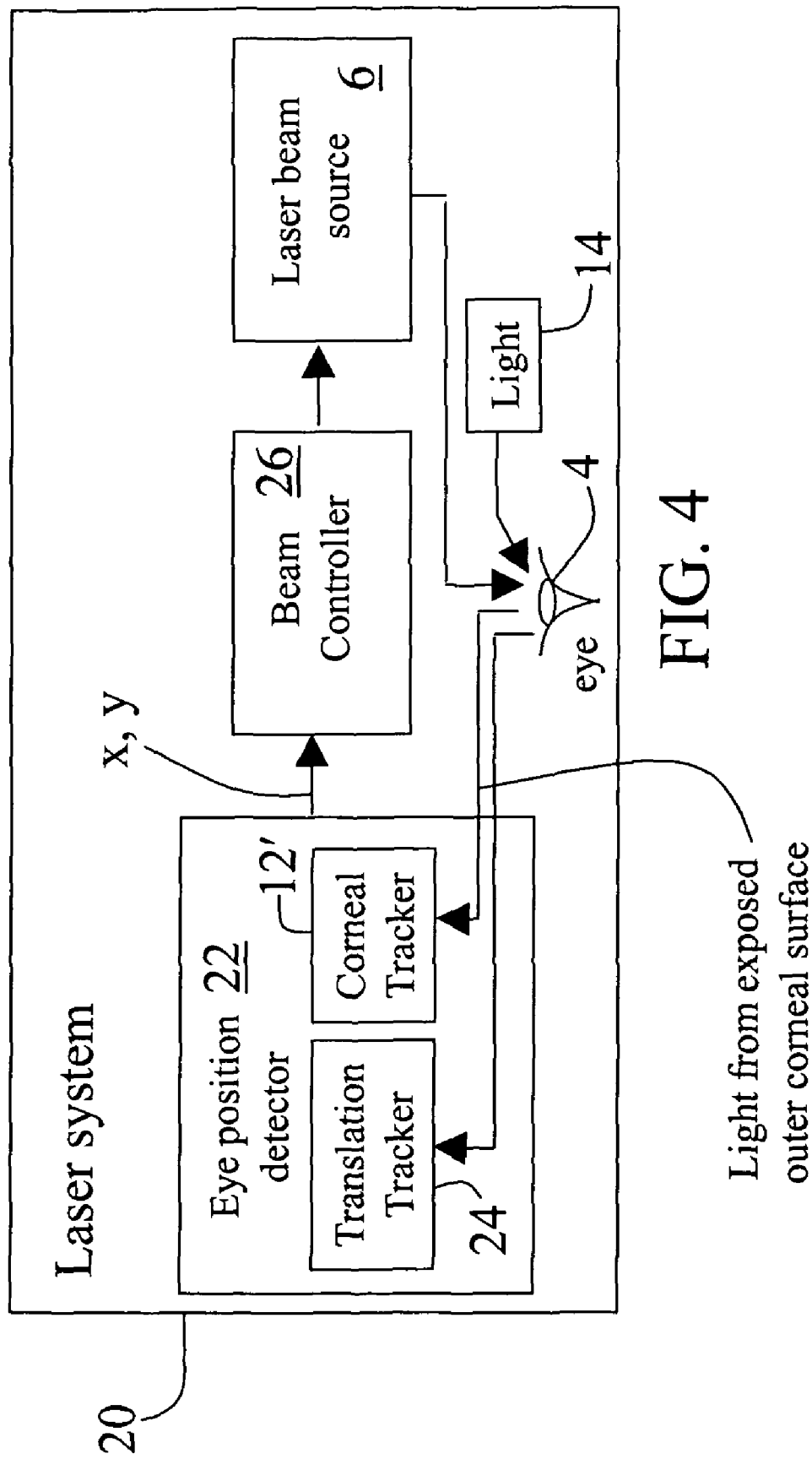
FIG. 4 is a block diagram of a laser system for eye treatment, the laser system having a corneal tracker and an eye translation tracker.

In an embodiment of the invention that makes use of prior techniques as well, referring to FIG. 4, a laser system 20 includes an eye position detector 22 that includes a translation tracker 24, the action of which is supplemented by the corneal tracker 12'. The beam controller 26 uses information from the eye position detector 22 to reference the pattern of placement of the laser beam 6. The translation tracker 24 uses light from the eye 4 to detect translation of features of the eye such as the iris and pupil, as in prior systems, or the translation tracker 24 may detect the translation of the intersection of the iris and the sclera. The eye position detector 22 compares the detected translation of the point reflections from the individual light sources on the cornea, derived from the corneal tracker 12', to the detected translation of the features by the translation tracker 24 to determine the translation of points on the outer surface of the cornea 56. As will be explained below, through this comparison, the roll of the eye 4 is sensed and provides a correction (x, y) to the position data obtained by the translation tracker 24. This position data is sent to the beam controller 26 that controls the position of the laser beam 6.

In some examples, the eye position detector 22 tracks the translation of the eye 4 by tracking the translation of the iris pupil boundary using detection of laser light reflected from the eye 4. In other examples, the eye position detector 22 tracks the translation of the eye 4 by image processing techniques to track the pupil using images of the eye 4.

Figure 4A:
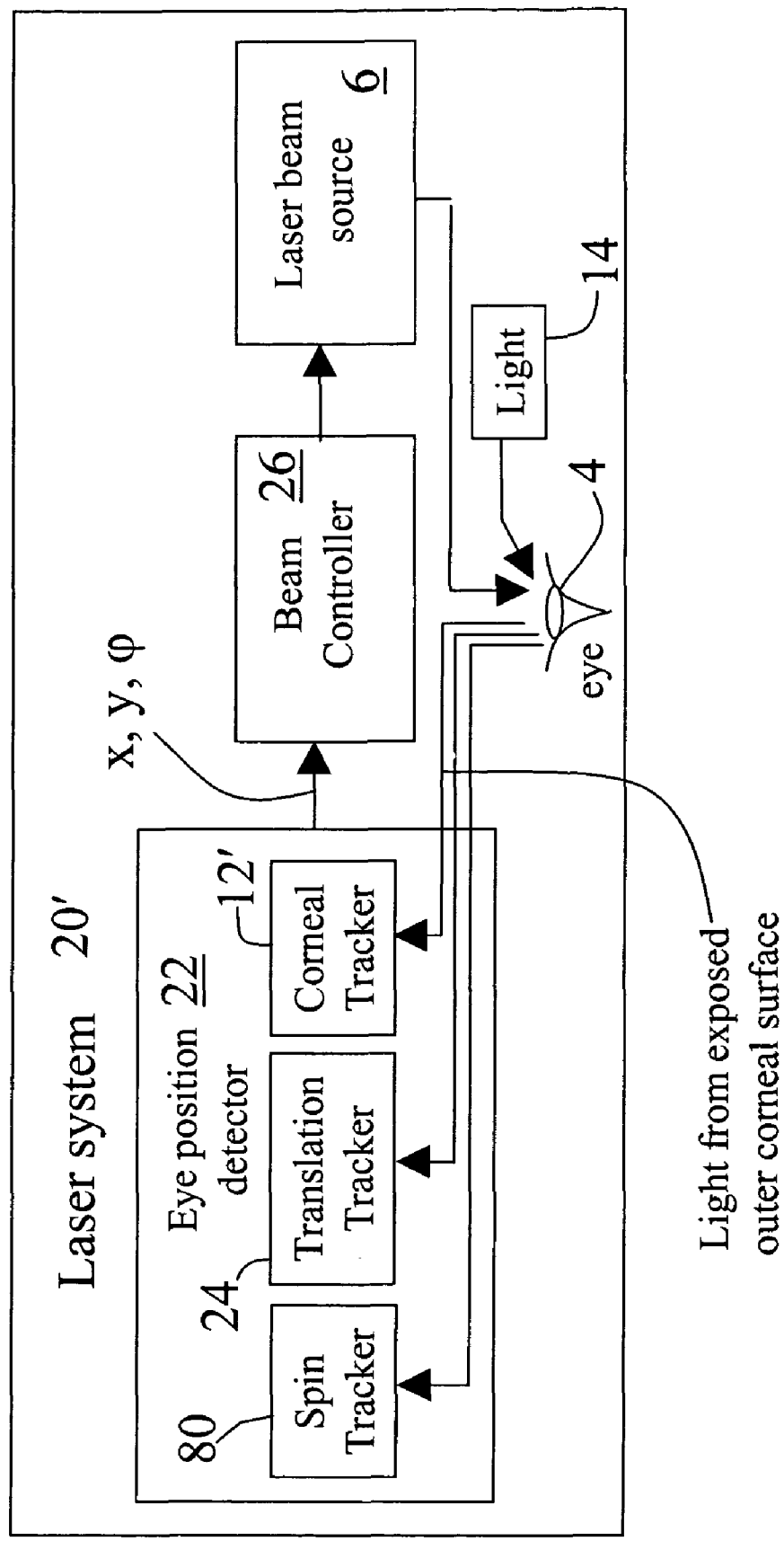
FIG. 4A is a block diagram of a laser system for eye treatment, the laser system having a spin tracker in addition to a corneal tracker and an eye translation tracker.

In an alternate embodiment of the laser system 20, referring to FIG. 4A, a laser system 20' includes the components of the laser system 20, and, in addition, a spin tracker 80. The spin tracker 80 uses light from the eye 4 to detect a spin angle ($\phi$) of the eye 4 by detecting rotation (about the eye's optical axis) of features of the eye 4 such as the iris 50. The measured spin ($\phi$) of the eye 4 is included in the information sent to the beam controller 26. In some examples, the spin tracker 80 tracks the spin of the eye 4 by image processing techniques that measure the rotation of features of the iris 50 about the optical axis of the eye 4.

Figure 4B:
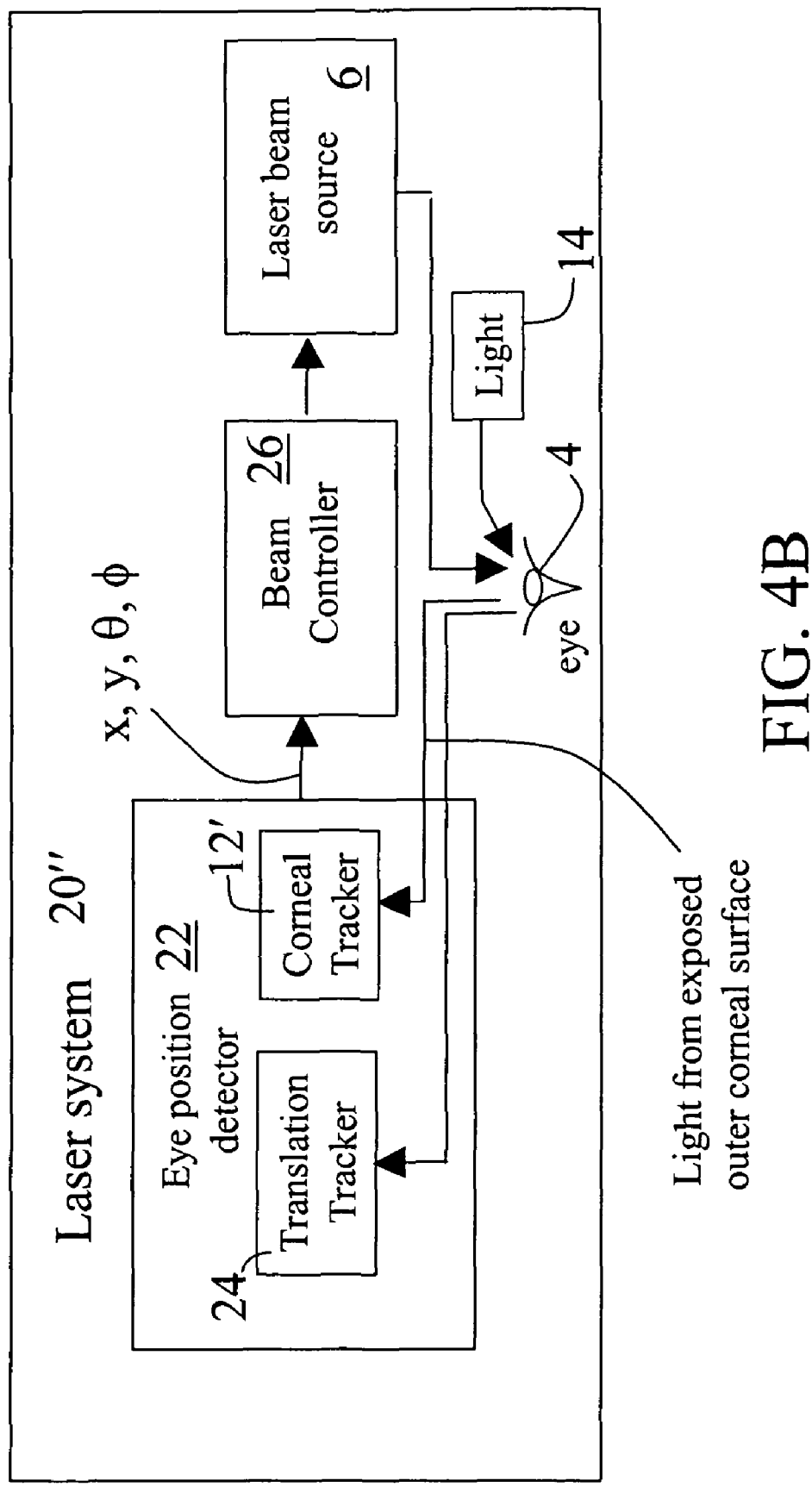
FIG. 4B is a block diagram of another laser system for eye treatment, the laser system having a side to side and up to down tracker.

In another alternate embodiment of the laser system 20, referring to FIG. 4B, a laser system 20" includes the components of the laser system 20. The corneal tracker 12' in the laser system 20" determines the roll of the eye 4 from side to side ($\theta$) and up to down ($\phi$). The eye position tracker 22 sends the combined position (x, y) and roll ($\theta$, $\phi$) information to the beam controller 26. The beam controller 26 responds to the measured rolling rotation of the eye 4 to adjust laser energy being deposited based on a change in the angle of presentation of a target portion of the outer surface of the cornea 56 due to the rolling rotation ($\theta$, $\phi$).

Figures 5, 5A:
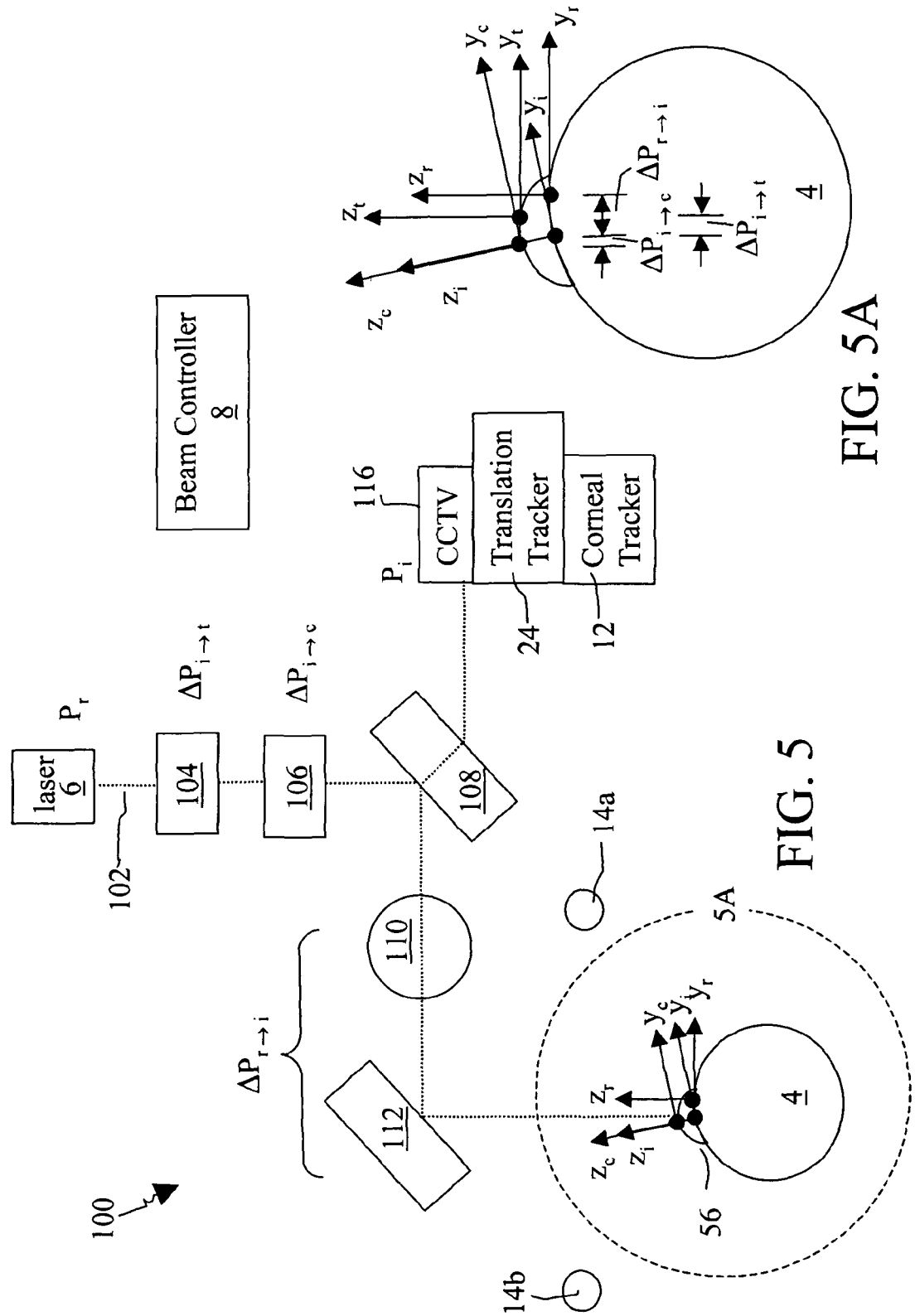
FIG. 5 is an optical path diagram of a laser system for eye treatment.
FIG. 5A is a magnification of a portion of FIG. 5.

Referring to FIGS. 5 and 5A, a laser system 100 is an implementation of the laser system 20. The laser system 100 includes a laser beam source 6 that emits a laser beam 102 for eye treatment. The path of the laser beam 102 is offset along X and Y coordinate axes that are orthogonal to the optical axis Z to track detected movement of the eye 4 along X and Y coordinate axes. The path of the laser beam 102 is also offset along X and Y axes to move to different target areas on the cornea 56. As illustrated, the laser beam 102 is offset along the Y coordinate axis by a X-Y translation system 104, a X-Y translation system 106, and X-Y translation mirrors 110, 112. The beam controller 8 controls the systems 104, 106, and mirrors 110, 112. The laser beam 102 is also reflected from dichroic mirror 108. A closed circuit television (CCTV) camera 116 collects light that reflects from the eye 4 from light sources 14a, 14b as well as from other light sources.

In one example, the translation of the iris/pupil boundary of the eye 4 is tracked using processed digital images from the CCTV camera 116. Standard image processing techniques are used to calculate the center of the iris/pupil boundary from the detected boundary. The iris/sclera boundary can also be used to calculate the center of the eye using image processing techniques. In other examples, the center of the iris can be tracked using pattern recognition of the visual features of the iris 50. In these examples, the translation tracker 24 can be enhanced with the spin tracker 80 by including tracking the rotation of the visual features of the iris 50 about the optical axis of the eye 4.

In another example, the translation of the iris/pupil boundary of the eye 4 is tracked using a measured reflection from the eye of infrared lasers. In other examples, the iris/sclera boundary can be tracked using the measured reflection of infrared lasers.

These translation-tracking techniques allow the system 100 to determine the translation of the iris/pupil or iris/sclera boundaries along the Y axis (or X axis, not shown) relative to a nominal position. A center point between these boundaries is the center of the eye 4. If the eye 4 is rolled by an angle θ, then the center of the anterior surface of the cornea 56 is offset from the center point between the boundaries.

The reference coordinate system for the nominal position of the eye 4 is $x_r$ (not shown), $y_r$, and $z_r$. The detected center of the iris/pupil boundary or the iris/sclera boundary coincides with the coordinate system $x_i$ (not shown), $y_i$, and $z_i$. The detected center of the cornea coincides with the coordinate system $x_c$ (not shown), $y_c$, and $z_c$.

The translation tracker 24 determines changes in translation of the coordinate system $x_i$, $y_i$. The integration of these changes is an X, Y translation from coordinate system $x_r$, $y_r$ to coordinate system $x_i$, $y_i$ or $\Delta P_{r \to i}$. The beam controller 8 receives the changes from the translation tracker 24 and sends control signals to adjust the mirrors 110, 112.

The mirrors 110, 112 modify the path of the laser beam 102 with the offset $\Delta P_{r \to i}$. The mirrors 110, 112 also modify the path of light reflecting from the eye 4 and arriving at the CCTV camera 116 with the offset $\Delta P_{r \to i}$. In one example, the mirrors 110, 112 also modify the path of infrared laser light from the eye 4 to measure the iris/pupil or iris/sclera boundaries with the offset $\Delta P_{r \to i}$. The translation changes detected by the translation tracker 24 are sent to modify the angles of the mirrors 110, 112. This results in the offset $\Delta P_{r \to i}$.

The corneal tracker 12' uses digital image processing techniques to determine the positions, relative to the coordinate system $x_i$, $y_i$, of the reflections of the lights from light sources 14a, 14b on the anterior surface of the cornea 56. From these positions, a middle point between the positions can be computed. The corneal tracker 12' uses these positions to determine a X, Y translation from coordinate system $x_i$, $y_i$ to coordinate system $x_c$, $y_c$ or $\Delta P_{i \to c}$. This is described in more detail below. The beam controller 8 receives the $\Delta P_{i \to c}$ information from the corneal tracker 12' and sends control signals to the X, Y translation system 106.

The X, Y translation system 106 receives signals from the corneal tracker 12' to modify the path of the laser beam 102 with the offset $\Delta P_{i \to c}$. The X, Y translation system 106 includes two mirrors to offset the path of the laser beam 102 along the X and Y axes.

Prior to the treatment process by laser system 100, a user (e.g., a surgeon) specifies treatment positions for the laser beam. These treatment positions are recorded and specified with respect to the coordinate system $x_i$, $y_i$ or $\Delta P_{i \to t}$. During the treatment process by laser system 100, these treatment positions are sent to the beam controller 8. The beam controller 8 receives the $\Delta P_{i \to t}$ information and sends control signals to the X, Y translation system 104.

The X, Y translation system 104 receives signals from the beam controller 8 to modify the path of the laser beam 102 with the offset $\Delta P_{i \to t}$. The X, Y translation system 104 includes two mirrors to offset the path of the laser beam 102 along the X and Y axes.

The images received by the CCTV camera 116 can be displayed to a user during surgery. These images are stabilized according to features of the eye 4 that are posterior to the cornea 56 such as the iris/pupil or the iris/sclera boundaries.

Figure 5B:
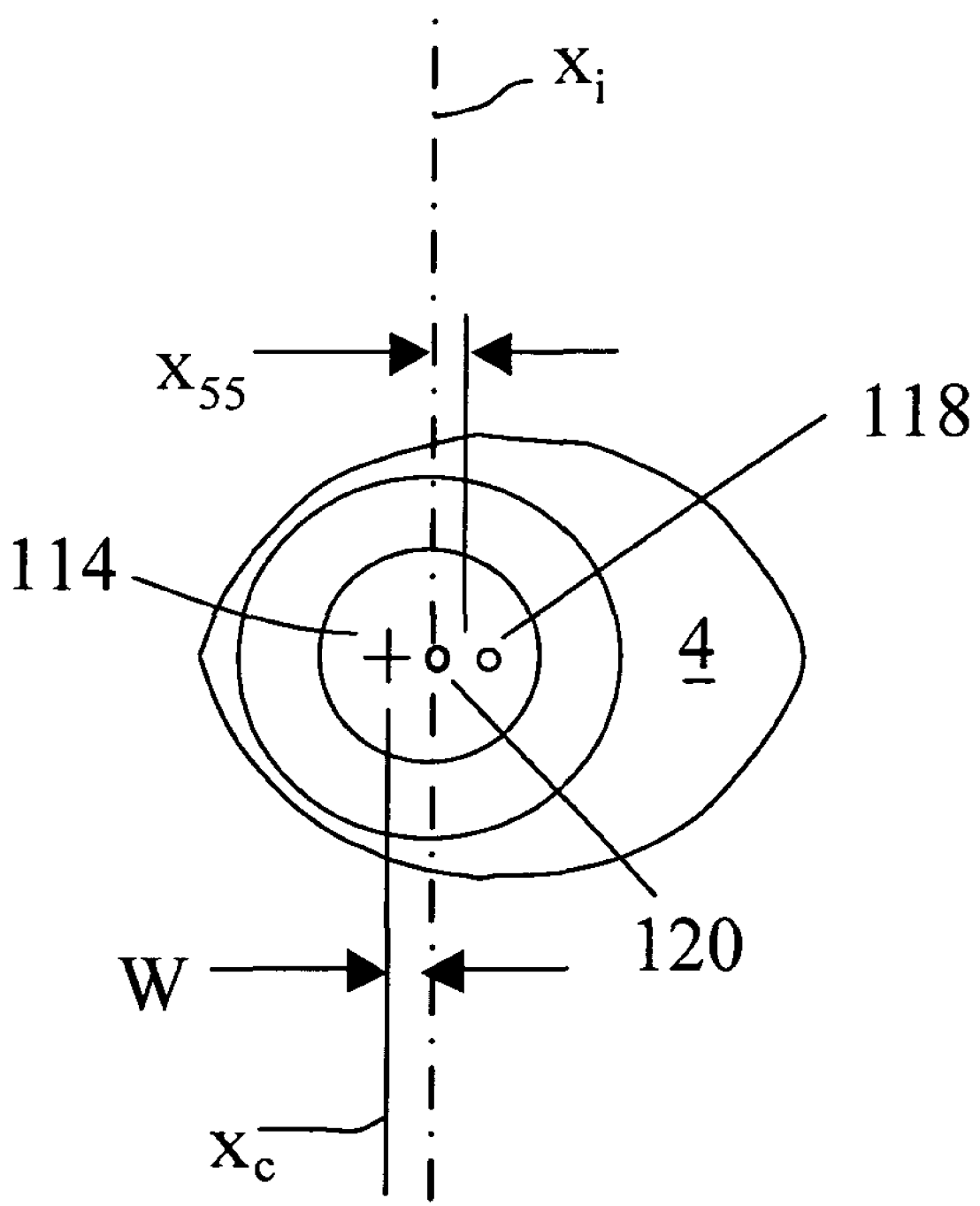
FIG. 5B is a diagram of a rolled eye with reflections from a corneal tracker.

Referring also to FIG. 5B, a distance W from the center of the pupil 52 to the center of the cornea 56 is calculated as follows. W is $\Delta P_{i \to c}$ along the $y_i$ axis. In this example, the eye 4 is rolled about axis $x_r$ by angle θ of 20 degrees. The CCTV camera 116 is a finite distance (when the eye 4 is not rolled, $z_2 - r_1$) from the surface of the cornea 56. The reflections of light 14a, 14b in the surface of the cornea 56 are 118, 120, respectively. The middle between the reflections 118, 120, as seen by the camera 116, is a measured distance $x_{55}$ from the center of the pupil 52 (coordinate system $x_i$, $y_i$).

Figure 6:
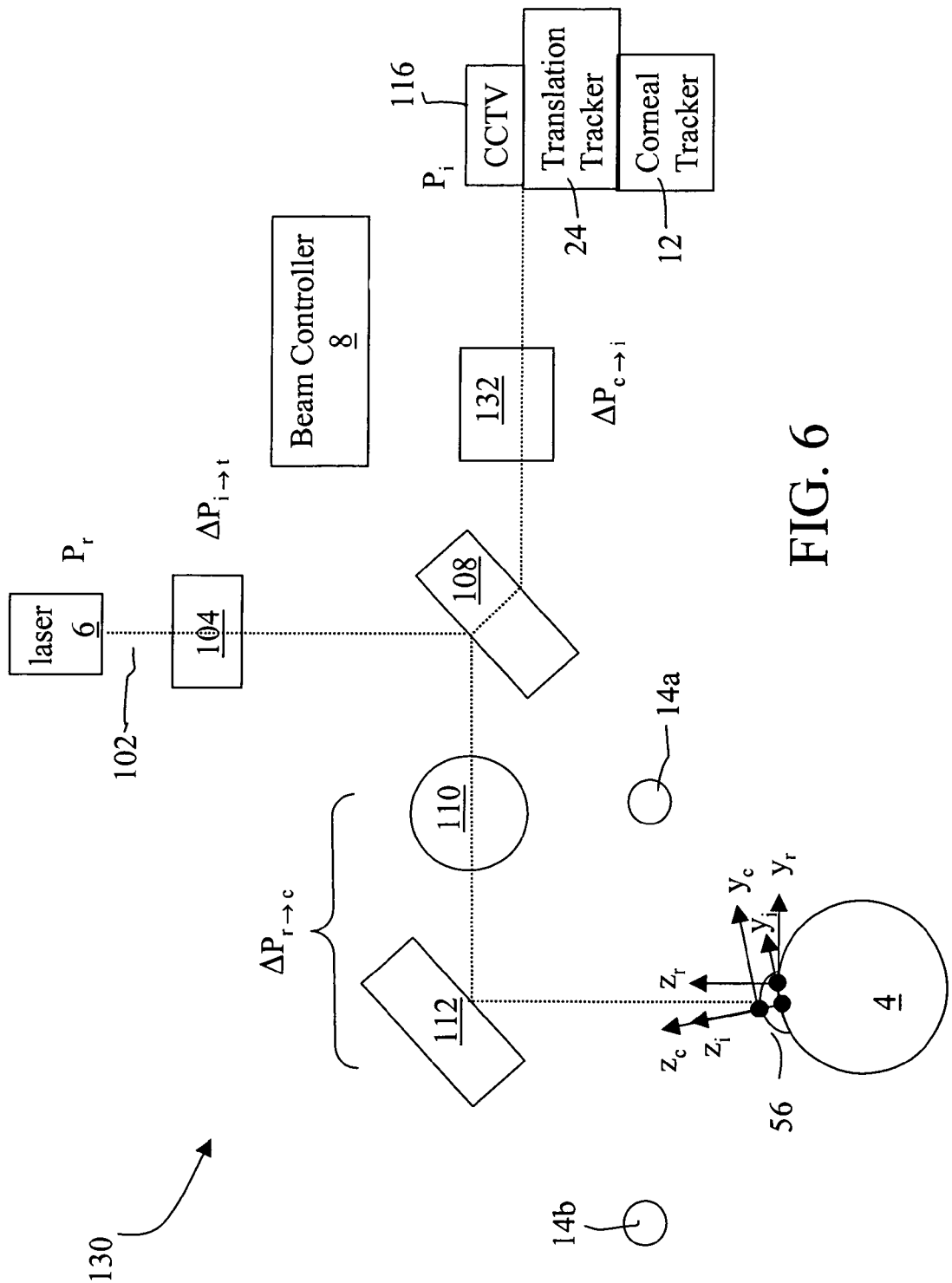
FIG. 6 is an optical path diagram of a laser system for eye treatment.

$W = B * x_{55}$, where $B = E - r_1 * F$
$C = 1/(G - H * I/J)$
$D = 1/(H - G * J/I)$
$E = 1/(I - J * G/H)$
$F = 1/(J - I * H/G)$
$G = z_2/(z_2 - r_2)$
$H = -z_2 * r_2/(z_2 - r_2)$
$I = (2 * x_9/r_3) * (z_2/(z_2 - r_1 + x_9))$
$J = -(r_1 - r_3) * I$ Referring to FIG. 6, a laser system 130 is another example of the laser system 20. The laser system 130 differs from the laser system 100 in that the mirrors 110, 112 offset the laser beam 102 by $\Delta P_{r \to c}$. To provide the translation tracker 24 and the corneal tracker 12' with an image stabilized with respect to features that are posterior to the cornea (e.g., pupil/iris or iris/sclera boundaries), an additional X, Y translation system 132 offsets the light reflected back from the cornea by $\Delta P_{c \to i}$. The offset $\Delta P_{r \to c}$ is calculated by the beam controller 8 by adding together offsets $\Delta P_{r \to i}$ (measured by the translation tracker 24) and $\Delta P_{i \to c}$ (measured by the corneal tracker 12'). The offset $\Delta P_{c \to i}$ is calculated by taking the negative of the offset $\Delta P_{i \to c}$ (measured by the corneal tracker 12'. The laser system 130 also provides a view to a user (e.g., a surgeon) via the CCTV camera 116 that is stabilized with respect to features that are posterior to the cornea.

Figure 7:
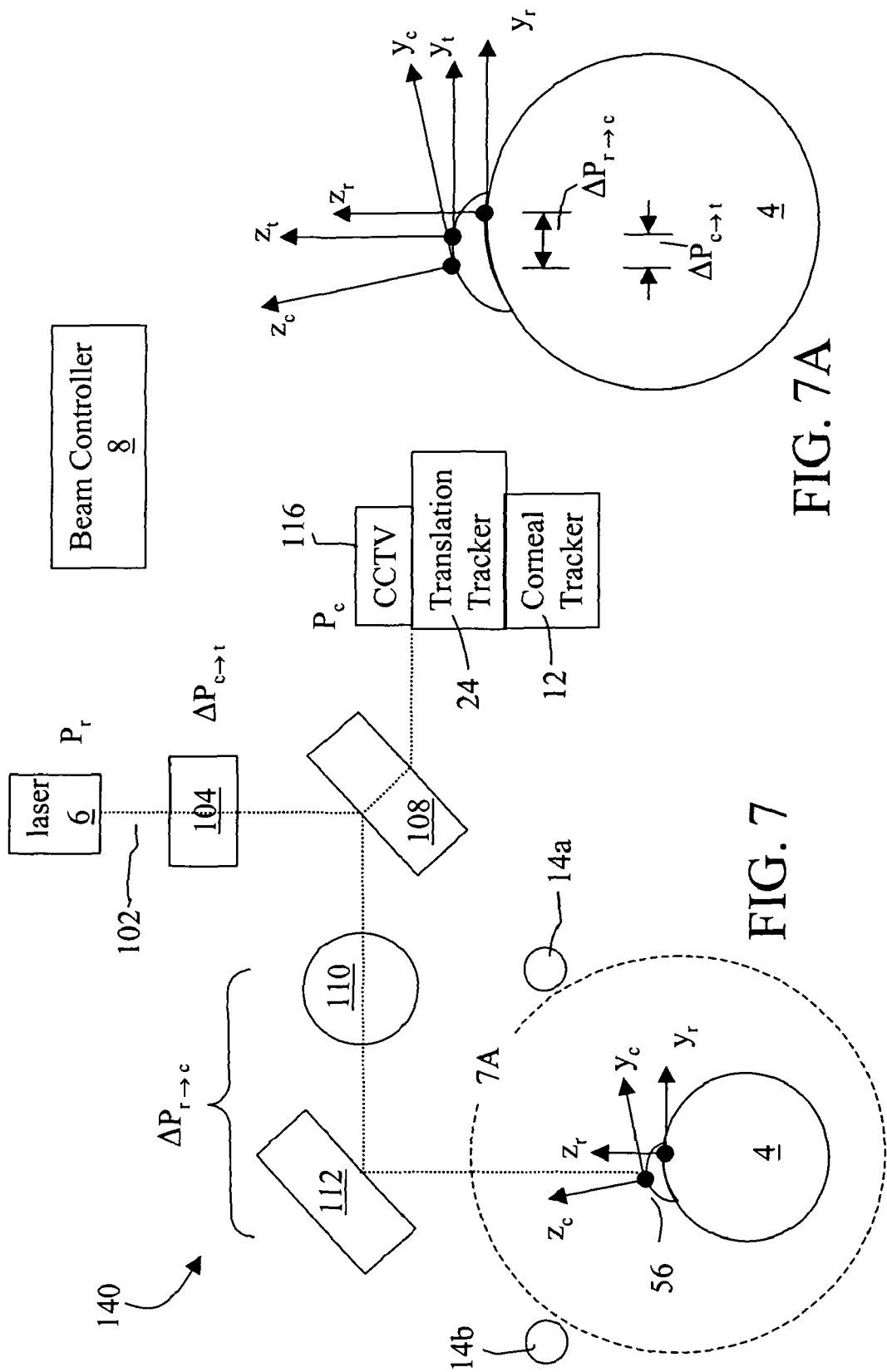
FIG. 7 is an optical path diagram of a laser system for eye treatment.

Referring to FIGS. 7 and 7A, a laser system 140 is another example of the laser system 20. The laser system 140 provides an image to the CCTV camera 116 that is stabilized with respect to the center of the cornea 56. The X, Y translation system 104 modifies the laser beam 102 by an offset $\Delta P_{c \to t}$. The mirrors 110, 112 modify the laser beam 102 by an offset $\Delta P_{r \to c}$. For the laser system 140, the beam controller 8 detects changes in the position of the center of the cornea 56 and sets the offset $\Delta P_{c \to t}$ according to these changes. The integral of these changes is the offset $\Delta P_{r \to c}$. For the laser system 140, the user (e.g., surgeon) sets target positions prior to the treatment process by specifying positions relative to the center of the cornea. These positions represent offsets $\Delta P_{r \to c}$. During the treatment process, the beam controller 8 sets different values of offset $\Delta P_{r \to c}$.

It is recognized that the radius of curvature $r_3$ of the cornea 56 may not stay constant during treatment of the eye 4. For example, treatment of the eye to reduce near sightedness or far sightedness can change the radius of curvature of the cornea 56. The reflections of lights 14a and 14b appear to be ½ the radius of curvature $r_3$ of the cornea 56 below the surface of the cornea 56. A typical value for $r_3$ is 8 millimeters, so the reflections appear to be 4 millimeters below the surface of the cornea 56. If this radius of curvature changes during treatment of the eye, the apparent distance from surface of cornea to image of light 14$a$ or 14$b$ will therefore also change.

During treatment of the eye 4, a worst case change in optical power of the surface of the cornea 56 is 10 diopters. Assuming that the index of refraction of the cornea is 1.35 and the nominal radius of curvature of the cornea 56 is 8 mm, the radius of curvature of the cornea can change from 6.5116 mm (due to +10 diopter change from nominal) to 10.3704 mm (due to −10 diopter change from nominal).

The following analysis of the effect of changing the corneal radius of curvature during tracking assumes that the change in radius of curvature from 8 to 6.5116 or 10.3704 mm is to be ignored during treatment and parameter B is calculated for the 8 mm case and held constant. Consider the case that the eye 4 rolls 20 degrees. The measured values for $x_{55}$ during treatment are for the nominal eye with $r_3$=8 mm, $x_{55}$=1.3777. For a +10 diopter change, $x_{55}$=1.8951 while for a −10 diopter change, $x_{55}$=0.5591. As stated previously, W=B*$x_{55}$. For the nominal eye with $r_3$=8 mm, B=−1.36814 so the correct value of W is (−1.36814)*1.3777=−1.8849 mm. For a +10 diopter change, B=−2.74229 while for a −10 diopter change, W=−0.76307. If we apply the values of B for the nominal eye to the +10 and −10 diopter cases we get the following incorrect values of W. For the +10 diopter case: W=−1.36814*1.8951=−2.5928, resulting in an error of −1.1510 mm in the estimation of W or the X or Y displacement of the center of the cornea 56 from the center of the pupil. For the −10 diopter case: W=−1.36814*0.5591=−0.7649, resulting in an error of +1.1200 mm in the estimation of W.

In many cases, it is desirable to achieve estimates of W from $x_{55}$ that have accuracies of 0.1 mm or less. Therefore, in these cases, it is useful to predict the changes in radius of curvature, $r_3$, of the cornea during surgery within about 1 diopter.

Another example of a corneal tracker 12, is a system that tracks, by pattern recognition, a computer-selected set of spaced apart fine detail visible artifacts in the corneal surface where the ablating laser 6 is not working, continually recording new patterns as the laser 6 forms them, and updating the reference region to a new region not being treated progressively as the ablating laser 6 reaches the area first serving as reference, e.g., as the ablating laser 6 courses through a spiral ablating pattern.

Figure 8:
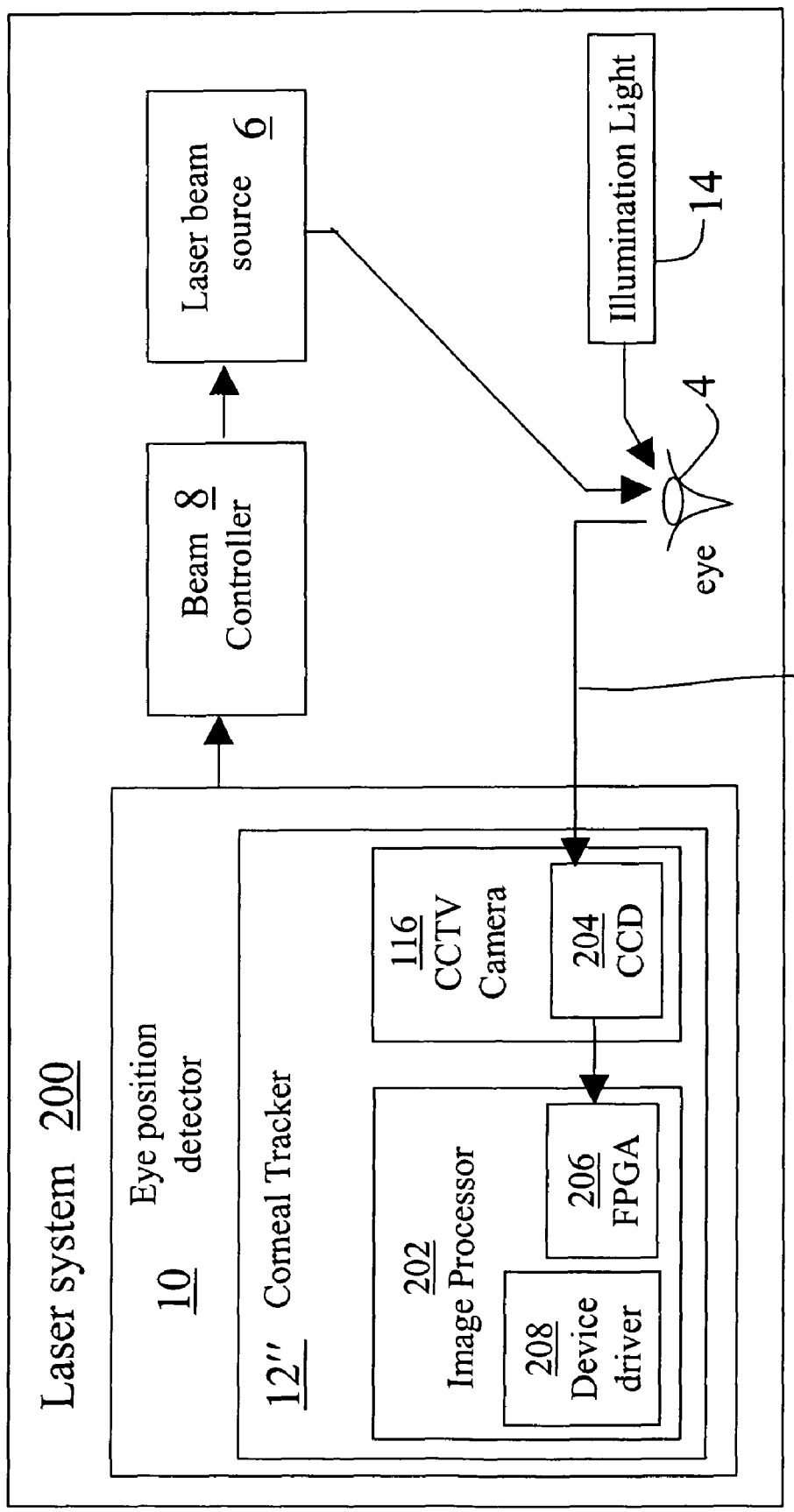
FIG. 8 is a block diagram of a laser system that includes a corneal tracker that uses image processing.

Referring to FIG. 8, a laser system 200 can be used for eye surgery involving surgery to the anterior surface of the cornea 56 after the top layer of the corneal epithelium (the "flap") is moved aside. The laser system 200 includes a corneal tracker 12". The corneal tracker 12" includes CCTV camera 116 and image processor 204. The image processor 204 is a computer with expansion capability and capable of executing instructions in a deterministic way, i.e., in real time. An example of the image processor 204 is a computer running the Windows NT® operating system. The corneal tracker 12" tracks motions of a set of selected microscopic details on the anterior (outer) surface of the cornea 56 exposed by turning the top layer of the corneal epithelium, the set of details defining a pattern in X and Y coordinates. During surgery, the original set of microscopic details is changed by the action of the laser 6, and is replaced by new sets while performing essentially in real time. This avoids the drawback that, capturing a complete image and analyzing it in detail requires at least a few milliseconds (and typically at least 50 milliseconds) with commercially available CCTV cameras. The motion of the eye 4 is so rapid that one needs to determine its position in less than about 1 millisecond. A summary of the literature on eye movement is given in the bachelor's thesis of Arne John Glenstrup and Theo Engell-Nielsen at the University of Copenhagen, available on the web at http://www.didku.dk/~/panic/eyegaze/article.html.

In one example, a set of separated, small regions of the rough surface are discovered and selected using image processing techniques. These regions have high visual contrast. These regions are not being currently sculpted by the laser 6. It may require 100 milliseconds to capture a full image and to identify these regions. A fast camera shutter that is open for only about 1 millisecond will ensure that this image is not blurred by eye motion. If the entire surface of the cornea 56 is to be sculpted by the laser 6, the laser system 20 sculpts at the left half of the cornea 56 while the right half is used for tracking, then pause for 100 milliseconds while high contrast features are found in the recently sculpted half, and then proceeds to sculpt at the right half while the left half is used for tracking, and so on.

A charge-coupled device (CCD) 204 is the photosensitive component of the CCTV camera 116. In one example, the CCD 204 for the CCTV camera 116 has small portions of its area read at very high speed. Techniques for examining two 8 by 8 pixel areas in a Texas Instruments TC 237 CCD 204 at a rate of 3000 samples per second are disclosed in "A High Frame Rate CCD Camera with Region-of-interest Capability", by Steve P. Monacos, Angel A. Portillo, William Liu, James W. Alexander, and Gerardo G. Ortiz, presented at the 2001 IEEE Aerospace Conference.

The scale of roughness of the surface of the cornea 56 under the top layer of the corneal epithelium is commonly between 5 and 50 microns. Having a 16 by 16 pixel area of the TC237 CCD 204 cover a 100 by 100 micron area on the cornea 56 enables the corneal tracker 12" to track one or more regions on the cornea 56. In one example, the TC237 CCD 204 has 658 by 496 pixels and covers a 4.1 by 3.1 millimeter area on the cornea 56, an area large enough to contain one or more small areas which are not being sculpted by the laser 6. In this example, each pixel in the TC237 204 measures 7.4 by 7.4 microns, so the lenses between the eye 4 and the TC237 CCD 204 must magnify the surface of the cornea 56 by approximately a factor of (16×7.4)/100=1.18. The optimum magnification can range from about 0.5 and 2.0.

The computational task of measuring the displacement of an image between two exposures may be implemented in various ways commonly known in the art. One technique is to calculate the convolution of the two successive images as a function of displacement between them. Assuming that the maximum displacement of the cornea in one millisecond is 50 microns, or 8 pixels. The total range of possible displacements ranges from −50 to +50 microns, or 16 pixels. The image processor 202 then calculates 16×16=256 convolutions of the overlapping portions of the two 16 by 16 pixel images. For example, when instructions for the image processor 202 are written in C and are executed on a 1.99 GHz Intel Xeon processor, 256 convolutions of the two 16 by 16 pixels images requires approximately 932 microseconds. If the area for image processing is reduced to 12 by 12 pixels, the time required is reduced to 311 microseconds.

In this example, an Altera 6000 series field programmable array (FPGA) 206 is used to control the TC237 CCD 204 from the image processor 202. In other examples, a TMS 320C40 digital signal processor can be used to control the TC237 CCD 204. The image process 202 includes a board (or daughter card) with either the Altera 6000 FPGA 206 or the TMS 320C40 digital signal processor. The Altera 6000 FPGA is available from the Altera Corporation of San Jose, Calif. A Windows NT device driver 208 is used to transfer data from the CCD 202 to the FPGA 206 on the image processor 202. The device driver 208 allows data to be transferred from the CCD to the computer in approximately a few tens of microseconds and then allows the convolution calculations to be started with a delay of a millisecond or less. The TC237 CCD 204 has an electronic fast shuttering capability so that no mechanical shutter is required.

Referring to FIGS. 9A-9C, one example of a surgery technique using the laser system 200 is illustrated by different temporal states 300, 320, and 340 of the cornea 56. The outer surface of the cornea 56 is divided into three different regions 56A, 56B, and 56C (shown magnified in FIGS. 9A-9C). During the state 300, the laser beam controller 8 controls the position of the laser beam 6 to perform surgery in an area 302 in region 56C. Meanwhile, the corneal tracker 12" tracks the position of the cornea 56 using discernable, possibly microscopic features in an area 304 in region 56B. Furthermore, the corneal tracker 12" also collects visual information from an area 306 in region 56A to recognize discernable features for future tracking in the next state 320. During the next state 320, the laser beam controller 8 controls the position of the laser beam 6 to perform surgery in an area 322 in the region 56B. Meanwhile, the corneal tracker 12" tracks the position of the cornea 56 using discernable, possibly microscopic features in an area 324 in the region 56A. Furthermore, the corneal tracker 12" also collects visual information from an area 326 in the region 56C to recognize discernable features for future tracking in the next state 340. During the next state 340, the laser beam controller 8 controls the position of the laser beam 6 to perform surgery in an area 342 in the region 56A. Meanwhile, the corneal tracker 12" tracks the position of the cornea 56 using discernable, possibly microscopic features in an area 344 in the region 56C. Furthermore, the corneal tracker 12" also collects visual information from an area 346 in the region 56B to recognize discernable, possibly microscopic features for future tracking in a next state.

A number of embodiments of the invention have been described. Nevertheless, it will be understood that various modifications may be made without departing from the spirit and scope of the invention. Accordingly, other embodiments are within the scope of the following claims.

What is claimed is:

1. A vision correction laser system for treating an eye having a cornea, the laser system comprising:
   a laser beam source capable of generating a laser beam for vision correction treatment;
   at least two spaced apart stationary light sources constructed to radiate toward the eye to produce a corresponding pattern of spaced apart light source reflected images from the outer surface of the anterior portion of the cornea, radially inward of the limbus, that is the target of the laser treatment, the light sources being spaced from the laser beam;
   an eye position detector which includes at least a corneal tracker, the eye position detector constructed to measure both rotation and translation of the eye;
   the corneal tracker including an image sensor having an imaging window that detects the pattern of spaced apart light source reflected images from the cornea radially inward of the limbus, and the corneal tracker constructed, by use of digital image processing of the sensed pattern of light source reflected images, to determine changes in the positions of the light source reflected images to measure rolling movement of the eye from side to side, angle theta (θ), and up to down, angle phi (φ); and
   a beam controller, the beam controller being responsive to the eye position detector to direct the laser beam with controlled energy from the laser beam source to a desired location on the eye.

2. The laser system of claim 1, wherein the laser beam source is constructed to produce a beam capable of ablating corneal tissue, the system having an array of at least three stationary spaced apart light sources arranged in a polygonal pattern to radiate toward the eye to produce a corresponding pattern of spaced apart light source reflected images from the outer surface of the anterior portion of the cornea the eye, radially inward of the limbus, in which the corneal tracker is adapted to determine the position of the center of the outer surface of the cornea, relative to an optical system, on the basis of determining the position of the centers of the distances between the detected images of at least three sets of two of the light sources in the array.

3. The laser system of claim 1, wherein the corneal tracker is constructed and arranged to measure rolled position side to side (θ) and up to down (φ) of the eye on the basis of spaced apart light source reflected images from the outer surface of the anterior portion of the cornea of the eye, radially inward of the limbus, produced by a pattern of light sources that are positioned to illuminate the cornea for visualization by the operator.

4. The laser system of claim 1, wherein the beam controller comprises a laser energy deposition controller, the laser energy deposition controller being constructed and arranged to deposit energy at selected levels at respectively designated positions on the anterior portion of the cornea, the deposition controller being responsive to measured side to side and up to down rolling rotation of the eye to correlate the level of energy deposition with side to side and up to down varying rolled positions of the eye.

5. The laser system of claim 4, wherein the laser system comprises a laser source, the laser source being fixed and the beam controller being constructed to respond to measured rolling rotation of the eye from side to side and up to down to adjust the level of energy being deposited based on change in the angle of presentation of a target portion of the corneal surface due to the rolling rotation.

6. The laser system of claim 1, wherein the eye position detector includes a translation tracker constructed and arranged to cooperate with the corneal tracker to adjust the aim of the laser beam.

7. The laser system of claim 6 constructed, in absence of side to side and up to down eye rolling rotation, to determine the position of the laser beam in response to the translation tracker.

8. The laser system of claim 6, wherein the translation tracker is an iris tracker that is constructed and arranged to track the translated position of the iris.

9. The laser system of claim 6, 7 or 8 further comprising an observation system having a display screen, the observation system enabling the operator to observe a display of the translation-determined position of the laser beam on an image of the cornea, the laser system comprising an offset arrangement to cause the point of incidence of the laser beam on the eye to be offset in X and Y coordinates, relative to the display screen, in an amount controlled by side to side and up to down rolling rotation data from the corneal tracking system.

10. The laser system of claim 6, 7 or 8, wherein, referring to X, Y and Z spatial coordinates in which Z represents the axis of the treatment beam, the translation tracker is adapted to produce X and Y beam control values and a visual representation of the aim of the laser beam relative to the iris, and the corneal tracker is responsive to side to side and up to down rolling rotation of the eye to produce X and Y corneal-rolling rotation-based control values representing the difference in true position of the desired treatment axis relative to its position approximated by the beam control values of the translation tracker, the laser system responsive to the beam control values of the translation tracker and corneal-side to side and up to down rolling rotation-based beam control values to direct the laser beam to a position on a portion of the outer surface of the anterior portion of the cornea that is offset from the visual representation of the aim of the laser beam relative to the iris.

11. The laser system of claim 10, wherein a pair of X, Y galvanometers controlled by the beam control values of the translation tracker are arranged to deflect the laser beam from the laser beam source, a beam splitter is arranged to direct portions of the deflected beam respectively toward the eye and toward an imaging device for the visual representation of the aim of the laser beam, and a second pair of X, Y galvanometers controlled by the corneal-rolling-rotation based beam control values of the corneal tracker are positioned to redirect one portion of the deflected beam to provide the offset due to side to side and up and down rolling rotation of the eye.

12. The laser system of claim 1, wherein there are at least three spaced apart light sources arranged in a polygonal pattern.

13. The laser system of claim 1 further comprising an iris tracker capable of producing an image of the iris and of the reflected pattern of spaced apart light sources, the laser system constructed and arranged so that, in the absence of side to side or up to down rolling rotation of the eye, translation movement of the eye does not substantially displace the image of the reflected pattern of light sources relative to the image of the iris.

14. The laser system of claim 8 or 13, wherein the iris tracker has dedicated scanners that detect the iris-to-pupil transition at least at three positions spaced about the periphery of the pupil, and is adapted to derive therefrom an estimated position for the center of the treatment.

15. The laser system of claim 8 or 13, wherein the iris tracker comprises an imager for imaging peripheral portions of the pupil and adjacent portions of the iris, and the iris tracker is adapted to derive from the imager an estimated position for the center of the treatment.

16. The laser system of claim 8 or 13, wherein the laser system is operative, in absence of side to side and up to down rolling rotation of the eye, to position the laser beam in response to the iris-translation tracker.

17. The laser system of claim 8 or 13, wherein the iris-translation tracker includes an imaging and pattern recognition system for imaging at least a portion of the iris in a plane, and the imaging and pattern recognition system estimates from a pattern of the image a position for the center of the treatment and an estimation of any rotation angle psi ($\psi$) of the iris in the plane.

18. The laser system of claim 1 in which the corneal tracker is adapted to use an estimated radius of curvature of the outer surface of the anterior portion of the cornea to produce X and Y control values based upon side to side and up to down rolling rotation of the eye and if the laser system changes the radius of curvature, the corneal tracker is adapted to update the estimated radius of curvature as the laser system changes the radius of curvature.

* * * * *